United States Patent
Su et al.

(10) Patent No.: US 8,989,861 B2
(45) Date of Patent: Mar. 24, 2015

(54) STIMULATION THERAPY FOR BLADDER DYSFUNCTION

(75) Inventors: Xin Su, Shoreview, MN (US); Dwight E. Nelson, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/701,603

(22) PCT Filed: Jun. 6, 2011

(86) PCT No.: PCT/US2011/039311
§ 371 (c)(1),
(2), (4) Date: Dec. 3, 2012

(87) PCT Pub. No.: WO2011/156286
PCT Pub. Date: Dec. 15, 2011

(65) Prior Publication Data
US 2013/0072998 A1    Mar. 21, 2013

Related U.S. Application Data

(60) Provisional application No. 61/352,179, filed on Jun. 7, 2010, provisional application No. 61/437,416, filed on Jan. 28, 2011.

(51) Int. Cl.
*A61N 1/36* (2006.01)
*A61B 5/0488* (2006.01)
(Continued)

(52) U.S. Cl.
CPC ........ *A61N 1/36007* (2013.01); *A61B 5/04882* (2013.01); *A61B 5/205* (2013.01);
(Continued)

(58) Field of Classification Search
USPC .......................................................... 607/41
See application file for complete search history.

(56) References Cited

U.S. PATENT DOCUMENTS

| 4,406,288 A | 9/1983 | Horwinski et al. |
| 5,919,216 A | 7/1999 | Houben et al. |

(Continued)

FOREIGN PATENT DOCUMENTS

| WO | 2006092007 A1 | 9/2006 |
| WO | 2009045297 A1 | 4/2009 |
| WO | 2010123704 A2 | 10/2010 |

OTHER PUBLICATIONS

Office Action from U.S. Appl. No. 13/701,690 dated Nov. 7, 2013, 15 pp.

(Continued)

*Primary Examiner* — Carl H Layno
*Assistant Examiner* — Erin Piateski
(74) *Attorney, Agent, or Firm* — Shumaker & Sieffert, P.A.

(57) ABSTRACT

A medical system may include a control module and a therapy delivery module configured to generate and deliver electrical stimulation therapy to a patient. The control module may be configured to control the therapy delivery module to deliver electrical stimulation at a first stimulation intensity for a first time period, to deliver electrical stimulation at a second stimulation intensity for a second time period immediately following the first time period, and to deliver electrical stimulation at the first stimulation intensity for a third time period immediately following the second time period. The second stimulation intensity may be less than the first stimulation intensity. The electrical stimulation may elicit a first inhibitory physiological response during the first time period and a second inhibitory physiological response during the second time period. The second inhibitory physiological response may be greater than the first inhibitory physiological response.

14 Claims, 8 Drawing Sheets

(51) Int. Cl.
  *A61B 5/20* (2006.01)
  *A61B 5/00* (2006.01)
  *A61B 5/04* (2006.01)
  *A61B 5/11* (2006.01)
  *A61N 1/05* (2006.01)

(52) U.S. Cl.
  CPC ............ *A61B 5/4836* (2013.01); *A61B 5/0031* (2013.01); *A61B 5/04001* (2013.01); *A61B 5/1116* (2013.01); *A61N 1/0514* (2013.01)
  USPC .......................................................... 607/41

(56) References Cited

U.S. PATENT DOCUMENTS

| | | | |
|---|---|---|---|
| 5,984,854 | A | 11/1999 | Ishikawa et al. |
| 6,141,587 | A * | 10/2000 | Mower ............................. 607/9 |
| 6,393,323 | B1 | 5/2002 | Sawan |
| 7,689,276 | B2 * | 3/2010 | Dobak ............................. 607/2 |
| 2003/0100930 | A1 | 5/2003 | Cohen et al. |
| 2004/0162594 | A1 | 8/2004 | King |
| 2005/0065575 | A1 | 3/2005 | Dobak |
| 2006/0122660 | A1 * | 6/2006 | Boveja et al. ................... 607/40 |
| 2006/0161218 | A1 | 7/2006 | Danilov |
| 2006/0200205 | A1 | 9/2006 | Haller |
| 2007/0100387 | A1 | 5/2007 | Gerber |
| 2007/0100388 | A1 * | 5/2007 | Gerber ............................ 607/41 |
| 2009/0054950 | A1 * | 2/2009 | Stephens ......................... 607/41 |
| 2009/0118777 | A1 * | 5/2009 | Iki et al. ............................ 607/2 |
| 2009/0131993 | A1 | 5/2009 | Rousso et al. |
| 2009/0138061 | A1 | 5/2009 | Stephens |
| 2009/0264955 | A1 | 10/2009 | Giftakis et al. |
| 2009/0264956 | A1 | 10/2009 | Rise et al. |
| 2009/0264957 | A1 | 10/2009 | Giftakis |
| 2009/0264967 | A1 | 10/2009 | Giftakis et al. |
| 2009/0306460 | A1 * | 12/2009 | Stephens et al. ................ 600/30 |
| 2010/0076254 | A1 | 3/2010 | Jimenez et al. |

OTHER PUBLICATIONS

International Search Report for international application No. PCT/US2011/039311, dated Sep. 3, 2012, 6 pp.
International Preliminary Report on Patentability from international application No. PCT/US2011/039311, dated Dec. 10, 2012, 13 pp.
Office Action for U.S. Appl. No. 13/701,654, dated Oct. 29, 2013, 9 pages, Considered OA for U.S. Appl. No. 13/701,654.
Final Office Action from U.S. Appl. No. 13/701,690, dated Apr. 23, 2014, 14 pp.
Notice of Appeal for U.S. Appl. No. 13/701,654, dated Jun. 26, 2014, 1 pp.
Pre-Appeal Brief Request for Review for U.S. Appl. No. 13/701,654, dated Jun. 26, 2014, 5 pp.
Response to Office Action dated Oct. 29, 2013, from U.S. Appl. No. 13/701,654, filed Jan. 29, 2014, 10 pages.
Response to Office Action dated Nov. 7, 2013, from U.S. Appl. No. 13/701,690, filed Feb. 7, 2014, 14 pages.
Response to Office Action dated Apr. 23, 2014, from U.S. Appl. No. 13/701,690, dated Jul. 22, 2014, 16 pp.
Office Action from U.S. Appl. No. 13/701,690, dated Sep. 24, 2014, 16 pp.
Examiner's Answer from U.S. Appl. No. 13/701,654, dated Sep. 25, 2014, 12 pp.
Response to Office Action dated Sep. 24, 2014, from U.S. Appl. No. 13/701,690, dated Dec. 22, 2014, 6 pp.
Reply Brief in Response to Examiner's Answer dated Sep. 25, 2014, from U.S. Appl. No. 13/701,654, dated Nov. 24, 2014, 13 pp.

* cited by examiner

STIMULATION THERAPY FOR BLADDER DYSFUNCTION

TECHNICAL FIELD

The disclosure relates to implantable medical devices and, more particularly, medical devices for treatment of bladder dysfunction.

BACKGROUND

Bladder dysfunction, such as an overactive bladder, urgency, or urinary incontinence, are problems that may afflict people of all ages, genders, and races. Various muscles, nerves, organs and conduits within the pelvic floor cooperate to collect, store and release urine. A variety of disorders may compromise urinary tract performance, and contribute to an overactive bladder, urgency, or urinary incontinence. Some of the disorders may be associated with aging, injury or illness.

Urinary incontinence may include urge incontinence and stress incontinence. In some examples, urge incontinence may be caused by disorders of peripheral or central nervous systems that control bladder micturition reflexes. Some patients may also suffer from nerve disorders that prevent proper triggering and operation of the bladder, sphincter muscles or nerve disorders that lead to overactive bladder activities or urge incontinence. In some cases, urinary incontinence can be attributed to improper sphincter function, either in the internal urinary sphincter or external urinary sphincter. For example, aging can result in weakened sphincter muscles, which may cause incontinence. Nerves running though the pelvic floor stimulate contractility in the sphincter. An improper communication between the nervous system and the urethra or urinary sphincter can result in a bladder dysfunction, such as overactive bladder, urgency, urge incontinence, or another type of urinary incontinence.

SUMMARY

In general, the disclosure is directed to devices, systems, and techniques for managing bladder dysfunction, such as an overactive bladder, urgency, or urinary incontinence. In some examples, the devices, systems, and techniques described herein alternatively or additionally may be utilized to manage fecal urgency or fecal incontinence. In some examples, an implantable medical device (IMD) may implement the techniques described herein to deliver stimulation therapy to at least one nerve (e.g., a pelvic floor nerve) via at least one electrode electrically connected to the IMD. In some examples the IMD delivers the stimulation therapy at a stimulation intensity that elicits a first inhibitory physiological response related to voiding during a first time period when the IMD delivers the stimulation. According to some examples, the IMD may reduce a stimulation intensity or cease delivering the stimulation during a second time period that immediately follows the first time period. During the second time period, the stimulation may elicit a second inhibitory physiological response related to voiding and, for at least a portion of the second time period, the second inhibitory physiological response may be greater (e.g., more pronounced) than the first inhibitory physiological response. One example of an inhibitory physiological response related to voiding is a reduction in a frequency of contraction of a detrusor muscle in a patient, which may cause a decrease in frequency of bladder contractions. Reduction in frequency of bladder contractions may reduce urgency of voiding and may reduce urgency and/or urinary incontinence.

In one aspect, the disclosure is directed to a medical system that includes a therapy delivery module configured to generate and deliver electrical stimulation therapy to a patient and a control module. According to this aspect of the disclosure, the control module is configured to control the therapy delivery module to deliver electrical stimulation at a first stimulation intensity for a first time period, to deliver electrical stimulation at a second stimulation intensity for a second time period immediately following the first time period, and to deliver electrical stimulation at the first stimulation intensity for a third time period immediately following the second time period. The second stimulation intensity may be less than the first stimulation intensity. In some examples, each of the first time period, the second time period, and the third time period includes at least five minutes. The electrical stimulation may elicit a first inhibitory physiological response related to voiding in the patient during the first time period and elicit a second inhibitory physiological response related to voiding in the patient during the second time period. In some examples, the second inhibitory physiological response is greater than the first inhibitory physiological response.

In another aspect, the disclosure is directed to a method including, with an IMD, delivering electrical stimulation at a first stimulation intensity to a patient during a first time period, where the electrical stimulation elicits a first inhibitory physiological response related to voiding in the patient during the first time period, and where the first time period is at least about 5 minutes. According to this aspect of the disclosure, the method also includes, with the IMD, delivering electrical stimulation at a second stimulation intensity to the patient during a second time period immediately following the first time period, where the second stimulation intensity is less than the first stimulation intensity, where the electrical stimulation elicits a second inhibitory physiological response related to voiding in the patient during the second time period, where the second inhibitory physiological response is greater than the first inhibitory physiological response, and where the second time period is at least about 5 minutes. The method further may include, with the IMD, delivering electrical stimulation at the first stimulation intensity to the patient during a third time period immediately following the second time period.

In an additional aspect, the disclosure is directed to a computer-readable medium including instructions that cause a processor to control a therapy delivery module to deliver electrical stimulation at a first stimulation intensity to a patient during a first time period, where the electrical stimulation elicits a first inhibitory physiological response related to voiding in the patient during the first time period, and where the first time period is at least about 5 minutes. According to this aspect of the disclosure, the computer-readable medium also includes instructions that cause the processor to control the therapy delivery module to deliver electrical stimulation at a second stimulation intensity to the patient during a second time period immediately following the first time period, where the second stimulation intensity is less than the first stimulation intensity, where the ceased electrical stimulation elicits a second inhibitory physiological response related to voiding in the patient during the second time period, where the second inhibitory physiological response is greater than the first inhibitory physiological response, and where the second time period is at least about 5 minutes. In accordance with this aspect of the disclosure, the computer-readable medium further includes instructions that cause the processor to control the therapy delivery module to deliver electrical stimulation at the first stimulation intensity to the patient during a third time period immediately following the second time period.

In a further aspect, the disclosure is directed to a medical system including means for generating and delivering electrical stimulation therapy to a patient and means for controlling the means for generating and delivering electrical stimulation therapy to delivery electrical stimulation at a first stimulation intensity for a first time period, to delivery electrical stimulation at a second stimulation intensity for a second time period immediately following the first time period and to deliver electrical stimulation at the first stimulation intensity for a third time period immediately following the second time period. According to this aspect of the disclosure, the second stimulation intensity is less than the first stimulation intensity, each of the first time period, the second time period, and the third time period comprises at least five minutes. Additionally, in accordance with this aspect of the disclosure, the electrical stimulation elicits a first inhibitory physiological response related to voiding in the patient during the first time period, the electrical stimulation elicits a second inhibitory physiological response related to voiding in the patient during the second time period, and the second inhibitory physiological response is greater than the first inhibitory physiological response.

In another aspect, the disclosure is directed to a medical system that includes a therapy delivery module configured to generate and deliver electrical stimulation therapy to a patient and a control module. According to this aspect of the disclosure, the control module is configured to control the therapy delivery module to deliver electrical stimulation at a first stimulation intensity during a first time period, where the first time period includes at least about 5 minutes. The first stimulation intensity may be between about 50% and about 100% of a threshold stimulation intensity. The control module may be configured to control the therapy delivery module to deliver electrical stimulation at a second stimulation intensity during a second time period immediately following the first time period. The second stimulation intensity may be less than the first stimulation intensity. In some examples, the electrical stimulation elicits an inhibitory physiological response related to voiding in the patient during the second time period, and the second time period comprises at least about 5 minutes. Furthermore, the control module may be configured to control the therapy delivery module to deliver electrical stimulation at the first stimulation intensity during a third time period immediately following the second time period.

In an additional aspect, the disclosure is directed to a method including, with an IMD, delivering electrical stimulation at a first stimulation intensity to a patient during a first time period, where the first time period comprises at least about 5 minutes. The first stimulation intensity may be between about 50% and about 100% of a threshold stimulation intensity. According to this aspect of the disclosure, the method also may include, with the IMD, delivering electrical stimulation at a second stimulation intensity during a second time period immediately following the first time period. The second stimulation intensity may be less than the first stimulation intensity. The second time period may include at least about 5 minutes. The electrical stimulation may elicit an inhibitory physiological response related to voiding in the patient during the second time period. The method also may include, with the IMD, delivering electrical stimulation at the first stimulation intensity during a third time period immediately following the second time period.

In another aspect, the disclosure is directed to a medical system that includes means for generating and delivering electrical stimulation therapy to a patient. According to this aspect of the disclosure, the medical system also includes means for controlling the means for generating and delivering electrical stimulation therapy that controls the means for generating and delivering electrical stimulation therapy to deliver electrical stimulation at a first stimulation intensity during a first time period, to deliver electrical stimulation at a second stimulation intensity during a second time period immediately following the first time period, and to deliver electrical stimulation at the first stimulation intensity during a third time period immediately following the second time period. The second stimulation intensity may be less than the first stimulation intensity. In some examples, the first time period comprises at least about 5 minutes. Additionally, in some examples, the first stimulation intensity is between about 50% and about 100% of a threshold stimulation intensity. According to this aspect of the disclosure, the electrical stimulation elicits an inhibitory physiological response related to voiding in the patient during the second time period. In some examples, the second time period is at least about 5 minutes.

In a further aspect, the disclosure is directed to a computer-readable medium comprising instructions that cause a processor to control a therapy delivery module to deliver electrical stimulation at a first stimulation intensity during a first time period, where the first stimulation intensity is between about 50% and about 100% of a threshold stimulation intensity, and where the first time period is at least about 5 minutes. In accordance with this aspect of the disclosure, the computer-readable medium also may include instructions that cause the processor to control the therapy delivery module to deliver electrical stimulation at a second stimulation intensity during a second time period immediately following the first time period, where the second stimulation intensity is less than the first stimulation intensity, where the electrical stimulation elicits an inhibitory physiological response related to voiding in the patient during the second time period, and where the second time period is at least about 5 minutes. According to this aspect of the disclosure, the computer-readable medium additionally may include instructions that cause the processor to control the therapy delivery module to deliver electrical stimulation at the first stimulation intensity during a third time period immediately following the second time period.

In another aspect, the disclosure is directed to an article of manufacture that includes a computer-readable storage medium. The computer-readable storage medium includes computer-readable instructions for execution by a processor. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, read only memory (ROM), or random access memory (RAM)) or any other type of volatile or non-volatile memory that stores instructions (e.g., in the form of a computer program or other executable) to cause a programmable processor to perform the techniques described herein.

The details of one or more example are set forth in the accompanying drawings and the description below. Other features, objects, and advantages will be apparent from the description and drawings, and from the claims.

DETAILED DESCRIPTION

Figure 1:
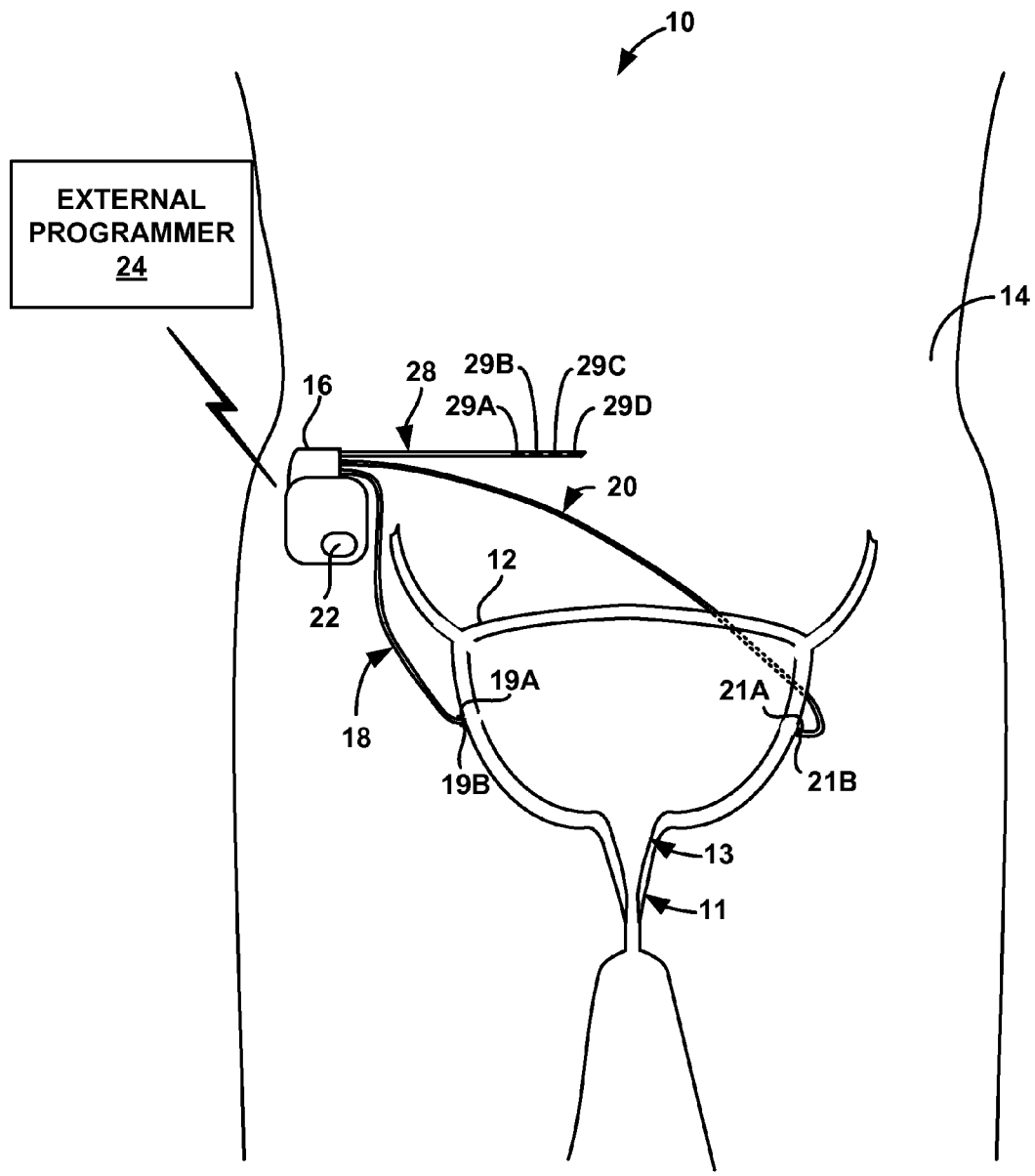
FIG. 1 is a conceptual diagram illustrating an example of a therapy system that delivers stimulation therapy to a patient to manage a bladder dysfunction, such as an overactive bladder, urgency, or urinary incontinence.

Bladder dysfunction refers to a condition of improper functioning of the bladder or urinary tract, and may include, for example, an overactive bladder, urgency, or urinary incontinence. Overactive bladder is a patient condition that may include symptoms, such as urgency, with or without urinary incontinence. Urgency is a sudden, compelling urge to urinate, and may often, though not always, be associated with urinary incontinence. Urinary incontinence refers to a condition of involuntary loss of urine, and may include urge incontinence, stress incontinence, or both stress and urge incontinence, which may be referred to as mixed urinary incontinence. As used in this disclosure, the term "urinary incontinence" includes disorders in which urination occurs when not desired, such as stress or urge incontinence.

One type of therapy for treating bladder dysfunction includes delivery of electrical stimulation to a target tissue site within a patient. For example, delivery of electrical stimulation from an implantable medical device to a spinal nerve, a sacral nerve, a pudendal nerve, dorsal genital nerve, a tibial nerve, an inferior rectal nerve, a perineal nerve, or branches of any of the aforementioned nerves may provide an effective therapy for bladder dysfunction. Electrical stimulation of the sacral nerve may modulate afferent nerve activities to restore urinary function. In addition, electrical stimulation of the nerves innervating pelvic floor muscles may strengthen pelvic floor muscle and promote urinary continence.

Some techniques described in this disclosure include delivering electrical stimulation according to a therapy program during a first time period. A therapy program defines respective values for a set of stimulation parameters with which an implantable medical device (IMD) generates and delivers electrical stimulation to a target tissue site in a patient. The set of stimulation parameters may define a first stimulation intensity. In some examples, an stimulation intensity may be a function of, for example, any combination of a current or voltage amplitude of the stimulation signal, the frequency of the stimulation signal, the shape of the stimulation signal, the duty cycle of the stimulation signal, the electrode combination used to deliver the stimulation signal, or other parameter values that may define the stimulation delivered to the patient. The electrical stimulation is delivered by an IMD via at least one electrode according to the therapy program. In some examples, the electrical stimulation is delivered at the first stimulation intensity during the first time period. In some examples, the stimulation may elicit a first therapeutic effect, such as a first inhibitory physiological response related to voiding in a patient during the first time period. In other examples, the electrical stimulation elicits substantially no therapeutic effect, such as no inhibitory physiological response related to voiding in a patient during the first time period.

While a therapeutic effect that is or includes an inhibitory physiological effect is primarily described herein, in other examples, another therapeutic effect related to bladder dysfunction may be elicited by the electrical stimulation described herein.

In some implementations, the IMD may deliver the electrical stimulation during the first time period at an intensity less than a threshold intensity level, which can be a physiological intensity threshold or a therapeutic intensity threshold. In some examples, the physiological intensity threshold level may be defined as the stimulation intensity at which an acute, physiologically significant response of a patient is first observed when increasing the stimulation intensity from a low intensity to a higher intensity. Stated another way, the physiological intensity threshold may be defined as approximately the lowest stimulation intensity that elicits an acute, physiologically significant response of the patient. In some examples, the physiological response may be different than the therapeutic response (e.g., an inhibitory physiological response) elicited by the delivery of electrical stimulation at the first stimulation intensity (or the second stimulation intensity, which is described below). The acute, physiologically significant response may or may not be perceived by the patient. In some examples, an acute response may be defined as a physiological response that occurs within about 30 seconds or less (e.g., about 10 seconds) of the patient receiving the stimulation (e.g., the initiation of the stimulation at the particular intensity level).

The acute physiological response that is used to determine the physiological intensity threshold may be manifest in a number of different examples. For example, the acute physiological response may be a motor response, a stimulation perception response, or a detected physiological response, such as a nerve action potential. A stimulation perception response may be observed and reported by the patient, e.g., as a paresthesia or other sensation. However, a motor response or a physiological response (e.g., a nerve impulse or non-therapeutic effect) may be reported by the patient, observed by a clinician, or automatically detected by one or more sensors internal or external to the patient. In some examples, whether a response is physiologically significant may be defined by the patient. For example, the stimulation may elicit movement of a toe of the patient, and the patient may define the movement of the toe as physiologically significant when the movement of the toe is perceptible or when the movement of the toe is above some arbitrary amount defined by the patient or the clinician.

In other examples, the threshold intensity level may be a therapeutic intensity threshold, or therapeutic threshold, in that the stimulation is insufficient to cause a desired therapeutic effect during delivery of stimulation (e.g., during the first time period). However, the stimulation is sufficient to cause the desired therapeutic effect after the stimulation is terminated (e.g., during the second time period). In some examples, this means that the electrical stimulation does not cause any significant therapeutic effect, or any therapeutic effects, during delivery stimulation (e.g., during the first time period). In other examples, however, the electrical stimulation may cause some detectable therapeutic effect during delivery of stimulation (e.g., during the first time period), but the therapeutic effect may be of a lesser magnitude than the desired therapeutic effect produced after termination of stimulation (e.g., during the second time period). As one example, if the desired therapeutic effect is a desired level of reduction in bladder contraction frequency, the stimulation may be insufficient to produce the desired therapeutic effect during delivery of stimulation (e.g., during the first time period) if it causes no therapeutic effect in reducing bladder contraction frequency or if it causes a level of therapeutic effect that is less than the desired level of reduction of bladder contraction frequency.

In summary, stimulation delivered according to some techniques described in this disclosure may be electrical stimulation insufficient to cause the desired therapeutic effect during delivery of stimulation (e.g., during the first time period), but sufficient to cause the desired therapeutic effect after stimulation is terminated (e.g., during the second time period). In some examples, the stimulation also may be insufficient to cause an acute physiological response, but sufficient to cause a desired therapeutic effect after stimulation is terminated. Selection of low intensity stimulation that is insufficient to cause the desired therapeutic effect during stimulation may be desirable to reduce power consumption, patient adaptation, and/or undesirable side effects associated with higher intensity stimulation.

The threshold intensity may be determined experimentally for each patient. An iterative stimulation procedure may be used to determine the threshold intensity. The iterative procedure may be performed by a clinician, for example, using the IMD implanted in the patient, or another device, or automatically by the IMD. In one example, a clinician may begin the determination of the threshold intensity level with a stimulation intensity that is not likely to produce any acute physiologically significant response, in the case of a physiological intensity threshold, or a therapeutic response from the patient, in the case of a therapeutic intensity threshold. This intensity may be selected, for example, based on the clinician's knowledge in some cases. The clinician can select the initial intensity by, for example, setting stimulation parameters (e.g., a current amplitude, a voltage amplitude, a frequency or pulse rate, a shape, a pulse width, a duty cycle, and/or the combination of electrodes) to produce a relatively low stimulation intensity and controlling the IMD to deliver stimulation to the patient using these parameters. Then, the clinician may incrementally increase one or more stimulation parameters, e.g., a current amplitude, pulse width, or pulse frequency, until an acute physiological response or therapeutic response to the stimulation is detected. Once the desired response is detected, the stimulation parameter may define the threshold intensity.

For example, in the case of a physiological intensity threshold, if no physiological response is observed in response to the stimulation at the initial intensity level, a value of one stimulation parameter may be changed to increase the stimulation intensity while the remaining parameters are kept approximately constant, and the IMD may be controlled to deliver stimulation at the new stimulation intensity. The stimulation parameter that is selected may be known to affect stimulation intensity. The process of modifying the stimulation parameter value and delivering stimulation according at the respective stimulation intensity level may be repeated until a threshold physiological response is observed (e.g., based on a signal generated by an implanted or external sensor or patient input indicating a perception of a physiological event). In this way, the process of finding the threshold intensity level may be an iterative procedure.

The threshold physiological response (also referred to herein as a "threshold response") may include a perception of the stimulation by the patient, or an observed response of a muscle that is driven by the nerve being stimulated at the target site, for example, a sphincter contraction, a toe twitch, or a detected signal on an electromyography (EMG). Other physiological responses may be detected when stimulating other nerves of the patient. In some examples, perception of the stimulation by the patient may occur prior to an observed response of a muscle that is being driven by the nerve being stimulated. In other words, the perception of the stimulation by the patient may occur at a lower threshold than the motor threshold. When stimulating one of the nerves described herein, such as a spinal nerve, sacral nerve, pudendal nerve, or the like, the physiological response may be a contraction of a toe of the patient, a flexing of an anal sphincter of the patient, or a detected signal on an EMG. Other physiological responses may be detected when stimulating other nerves of patient 12.

In one example, the threshold intensity level may be determined by setting the stimulation frequency at about 10 Hz to about 14 Hz and increasing the current amplitude until a muscle response is observed based on a sensor input (e.g., EMG indicating the muscle movement) or patient input (e.g., perception of the stimulation by the patient).

In some examples, based on the determined threshold stimulation intensity, the clinician may select the stimulation parameters that define the first stimulation intensity, for example, reducing one or more stimulation parameter values such that the selected stimulation parameters produce electrical stimulation having an intensity less than the threshold intensity. The clinician may reduce the intensity to any value as long as the resulting stimulation parameters are still sufficient to induce the post-stimulation, desired therapeutic effect (e.g., a reduction in bladder contraction frequency following initiation of stimulation at the first stimulation intensity), which is described in further detail below.

In some examples, the techniques for delivering therapy for managing bladder dysfunction further include delivering stimulation at a second stimulation intensity according to the therapy program during a second time period that immediately follows the first time period. The second stimulation intensity may be less than the first stimulation intensity. In some examples, the stimulation intensity may be reduced by, for example, reducing a voltage or current amplitude at which the stimulation is delivered. However, modification to other therapy parameter values (e.g., frequency) may also reduce stimulation intensity. In some examples, the IMD may cease delivering stimulation according to the therapy program or cease delivering any stimulation during the second time period, i.e., the reduced, second stimulation intensity may include not delivering stimulation to the patient. The stimulation may elicit a second inhibitory physiological response related to voiding in the patient during the second time period.

While not wishing to be bound by theory, the second inhibitory physiological response related to voiding may be elicited by the stimulation delivered at the first stimulation intensity during the first time period. Such an inhibitory physiological response will be referred to herein as post-stimulation inhibition, which may be, for example, a physiological response to stimulation which occurs or continues to occur after cessation of delivery of stimulation or reduction in stimulation intensity. In some examples, for at least a portion of the second time period the second inhibitory physiological response is greater than the first inhibitory physiological response. The clinician may select the stimulation parameters that define the second stimulation intensity stimulation by, for example, decreasing one or more stimulation parameter values such that the selected stimulation parameters produce electrical stimulation having an intensity less than the first stimulation intensity.

In some examples, the inhibitory physiological response related to voiding is a reduction in bladder contraction frequency. In such examples, the reduction in bladder contraction frequency during at least a portion of the second time period, when stimulation is not being delivered to the patient or is being delivered at a lower stimulation intensity, may be greater that the reduction in bladder contraction frequency during the first time period. In this way, the second inhibitory physiological response may be greater than the first inhibitory physiological response. In other words, bladder contraction frequency may be lower during at least a portion of the second time period than during at least a portion of the first time period.

In some examples, the techniques include delivering a first stimulation therapy and a second stimulation therapy. In some examples, the first stimulation therapy is a chronic (i.e., non-temporary) therapy and the second stimulation therapy is an acute therapy. The first stimulation therapy includes delivery of stimulation at a first stimulation intensity for a first time period, during which the stimulation elicits a first inhibitory physiological response, and delivering stimulation at a second stimulation intensity for a second time period immediately following the first time period, during which the stimulation elicits a second inhibitory physiological response that is greater than the first inhibitory physiological response. Again, the second stimulation intensity may be less than the first stimulation intensity, and the second stimulation intensity may include not delivering stimulation during the second time period in some examples. In addition, in some examples, the first stimulation therapy is delivered to a patient in an open loop manner, e.g., without the use of an external feedback mechanism such as input from a sensor. However, in some cases, a sensor signal or patient input may be used to adjust the stimulation parameters, such as the length of the first time period or the length of the second time period, of the first stimulation therapy.

The second stimulation therapy may be referred to as a temporary stimulation therapy because the second stimulation therapy is delivered for a predetermined period of time (duration of time), rather than on a regular basis. In some examples, the predetermined period of time may be controlled by the patient. In addition, in some examples, the second stimulation therapy may be referred to as functional electrical stimulation because the second stimulation therapy results in a movement of muscles of the patient that provides a specific functional result. For example, the second stimulation therapy may generate a contraction of the urinary or anal sphincter of a patient.

In other examples, the second stimulation therapy may include stimulation therapy similar to the first stimulation therapy, e.g., stimulation therapy that includes delivery of stimulation at a first stimulation intensity for a first time period, during which the stimulation elicits a first inhibitory physiological response, and delivering stimulation at a second stimulation intensity that is less than the first stimulation intensity for a second time period immediately following the first time period, during which the stimulation elicits a second inhibitory physiological response that is greater than the first inhibitory physiological response. In some examples, the IMD may deliver the second stimulation therapy according to stimulation parameter values that result in the second stimulation therapy being more efficacious than the first stimulation therapy. For example, the second stimulation therapy may be delivered at a higher intensity, for a longer first time period, and/or with a shorter second time period, which may result in the second stimulation therapy being more efficacious than the first stimulation therapy.

As used herein, when used with reference to the first and second stimulation therapies, the term "more efficacious" may refer to a more immediate inhibitory physiological effect, a greater inhibitory effect, or both. For example, the IMD may deliver the second stimulation therapy according to stimulation parameter values that produce a more immediate inhibitory physiological effect, i.e., the inhibitory physiological effect begins closer in time to the initiation of stimulation for the second stimulation therapy than for the first stimulation therapy. As an example, the IMD may deliver the second stimulation therapy to a dorsal nerve of the clitoris/penis at an intensity of about 0.8 threshold intensity level to generate a more immediate inhibition of bladder contractions relative to the first stimulation therapy.

As another example, the IMD may deliver the second stimulation therapy according to stimulation parameter values that produce a greater inhibitory physiological effect. For example, when the inhibitory physiological effect includes a reduction in bladder contraction frequency, the second stimulation therapy may reduce the bladder contraction frequency to a lower value than the first stimulation therapy. For example, the first stimulation therapy may reduce the bladder contraction frequency to between about 25% and about 50% of a baseline bladder contraction frequency (e.g., a frequency of bladder contractions when the patient is not experiencing therapeutic effects of stimulation therapy), and the second stimulation therapy may reduce the bladder contraction frequency to less than about 25% of the baseline bladder contraction frequency.

In some examples described herein, the second stimulation therapy is delivered to the patient in a closed loop or a pseudo-closed loop manner because the initiation of the delivery of the second stimulation therapy is dependent upon an occurrence of a trigger event, as described in further detail below. In addition, in some examples, the IMD delivers the first and second stimulation therapies according to different sets of stimulation parameters and/or to different target tissue sites within the patient. However, in some examples, the first and second stimulation therapies are delivered to the same nerve or to the same tissue site (e.g., the sacral or pudendal nerve).

In some examples, the IMD delivers the first stimulation therapy to an afferent fiber of a spinal nerve, a sacral nerve, a pudendal nerve, dorsal genital nerve, a tibial nerve, an inferior rectal nerve, a perineal nerve, or branches of any of the aforementioned nerves to inhibit bladder contractions (e.g., reduce a frequency of bladder contractions). In some examples, the IMD may deliver the second stimulation therapy to a hypogastric nerve, a pudendal nerve, a dorsal penile nerve in a male patient, a dorsal clitoral nerve in a female patient, or to the external urinary sphincter or any combination thereof to promote continence.

In some of the closed loop or a pseudo-closed loop therapy examples, the second stimulation therapy may be triggered when a patient condition indicative of an imminent involuntary voiding event or an increase in a possibility that the involuntary voiding event will occur is detected (e.g., by the IMD or a sensor separate from the IMD). The patient condition may be, for example, a bladder contraction. The bladder contraction may be detected via any suitable sensing mechanism or under the control of the patient. For example, the IMD may detect bladder contraction based on bladder impedance, bladder pressure, pudendal or sacral afferent nerve signals, external urinary sphincter or anal sphincter EMG, motion sensor signals (e.g., accelerometer signals), or any combination thereof.

In other examples, the trigger event for activating the delivery of the second stimulation therapy may be patient input. In some examples described herein, the patient may use a medical device programmer or another input mechanism to trigger the IMD to deliver the second stimulation therapy. In some examples, the patient may also use the programmer to manually abort the delivery of the second stimulation therapy. In such examples, the IMD may wirelessly communicate with the programmer to alert that patient of prospective delivery of the second electrical stimulation. In additional examples, the patient may use the programmer to prevent or abort the second electrical stimulation therapy during voluntary voiding events.

Although the techniques are primarily described in this disclosure for managing bladder dysfunction, the techniques may also be applied to manage fecal urgency or fecal incontinence. In fecal incontinence examples, the IMD delivers the second stimulation therapy when patient input is received, when a patient parameter indicative of an imminent fecal incontinence event is detected or when a patient parameter indicative of an increased probability of an occurrence of a fecal incontinence event is detected (e.g., an increased patient activity level). The patient parameter may include, for example, contraction of the anal sphincter, patient activity level or patient posture state. The IMD may use any suitable sensing mechanism to detect contraction of the anal sphincter, such as a pressure sensor or an EMG sensor.

FIG. 1 is a conceptual diagram that illustrates an example of a therapy system 10 that delivers electrical stimulation therapy to generate an inhibitory physiological response related to voiding in patient 14 to manage a bladder dysfunction of patient 14. As described above, the stimulation therapy may include delivery of stimulation at a first stimulation intensity during a first time period and delivery of stimulation at a second stimulation intensity that is less than the first stimulation intensity during a second time period immediately following the first time period. As described above, the second stimulation intensity may include substantially no stimulation intensity, i.e., in some examples, delivering stimulation at the second stimulation intensity may include ceasing delivery of stimulation during the second time period. For sake of conciseness, the description herein will be directed primarily to ceasing delivery of stimulation during the second time period. However, it will be appreciated that the various examples of techniques described herein may include delivering stimulation at a first, higher intensity during the first time period and delivering stimulation at a second, reduced stimulation intensity during the second time period.

The stimulation therapy may elicit an inhibitory physiological response related to voiding during the second time period, and may or may not elicit an inhibitory physiological response related to voiding during the first time period. Regardless of whether an inhibitory physiological response related to voiding is elicited during the first time period, the inhibitory physiological response is greater for at least a portion of the second time period than during the first time period. In some examples, the inhibitory physiological response includes a reduction in bladder contraction frequency.

Therapy system 10 includes an IMD 16, which is coupled to leads 18, 20, and 28 and sensor 22. System 10 also includes an external programmer 24, which communicates with IMD 16 via a wireless communication protocol. IMD 16 generally operates as a therapy device that delivers electrical stimulation to, for example, a target tissue site proximate a spinal nerve, a sacral nerve, a pudendal nerve, dorsal genital nerve, a tibial nerve, an inferior rectal nerve, a perineal nerve, or branches of any of the aforementioned nerves. IMD 16 provides electrical stimulation therapy to patient 14 by generating and delivering a programmable electrical stimulation signal (e.g., in the form of electrical pulses or an electrical waveform) to a target therapy site near lead 28 and, more particularly, near electrodes 29A-29D (collectively referred to as "electrodes 29") disposed proximate to a distal end of lead 28.

IMD 16 may be surgically implanted in patient 14 at any suitable location within patient 14, such as near the pelvis. In some examples, IMD 16 may be implanted in a subcutaneous location in the side of the lower abdomen or the side of the lower back or upper buttocks. IMD 16 has a biocompatible housing, which may be formed from titanium, stainless steel, a liquid crystal polymer, or the like. The proximal ends of leads 18, 20, and 28 are both electrically and mechanically coupled to IMD 16 either directly or indirectly, e.g., via respective lead extensions. Electrical conductors disposed within the lead bodies of leads 18, 20, and 28 electrically connect sense electrodes (e.g., electrodes 19A, 19B, 21A, and 21B) and stimulation electrodes, such as electrodes 29, to a sensing module and a therapy delivery module (e.g., a stimulation generator) within IMD 16. In the example of FIG. 1, leads 18 and 20 carry electrodes 19A, 19B (collective referred to as "electrodes 19") and electrodes 21A, 21B (collectively referred to as "electrodes 21"), respectively. As described in further detail below, electrodes 19 and 21 may be positioned for sensing an impedance of bladder 12, which may increase as the volume of urine within bladder 12 increases.

One or more medical leads, e.g., leads 18, 20, and 28, may be connected to IMD 16 and surgically or percutaneously tunneled to place one or more electrodes carried by a distal end of the respective lead at a desired nerve or muscle site, e.g., one of the previously listed target therapy sites such as a tissue site proximate a spinal, sacral or pudendal nerve. For example, lead 28 may be positioned such that electrodes 29 deliver a stimulation therapy to a spinal, sacral or pudendal nerve to reduce a frequency of contractions of bladder 12. In some examples, lead 28 may also deliver a second stimulation therapy to a hypogastric nerve, a pudendal nerve, a dorsal penile/clitoral nerve, the urinary sphincter, or any combination thereof to a promote closure of a urinary sphincter of patient 14. In some examples, lead 28 may also deliver a second stimulation therapy to spinal, sacral or pudendal nerve to reduce a frequency of contractions of bladder 12. Electrodes 29 of the common lead 28 may deliver stimulation to the same or different nerves. In FIG. 1, leads 18 and 20 are placed proximate to an exterior surface of the wall of bladder 12 at first and second locations, respectively. In other examples of therapy system 10, IMD 16 may be coupled to more than one lead that includes electrodes for delivery of electrical stimulation to different stimulation sites within patient 14, e.g., to target different nerves.

In the example shown in FIG. 1, leads 18, 20, 28 are cylindrical. Electrodes 19, 20, 29 of leads 18, 20, 28, respectively, may be ring electrodes, segmented electrodes, partial ring electrodes or any suitable electrode configuration. Segmented and partial ring electrodes each extend along an arc less than 360 degrees (e.g., 90-120 degrees) around the outer perimeter of the respective lead 18, 20, 28. In some examples, segmented electrodes 29 of lead 28 may be useful for targeting different fibers of the same or different nerves to generate different physiological effects for first and second stimulation therapies. As described in further detail below, in some examples, segmented electrodes may be utilized deliver relatively high frequency stimulation (e.g., about 66 Hertz) and relatively low frequency stimulation (e.g., about 15 Hertz) to activate both fast twitch muscles and low twitch muscles substantially simultaneously or during alternating time periods. In examples, one or more of leads 18, 20, 28 may be, at least in part, paddle-shaped (e.g., a "paddle" lead), and may include an array of electrodes on a common surface, which may or may not be substantially flat.

In some examples, one or more of electrodes 19, 20, 29 may be cuff electrodes that are configured to extend at least partially around a nerve (e.g., extend axially around an outer surface of a nerve). Delivering stimulation via one or more cuff electrodes and/or segmented electrodes may help achieve a more uniform electrical field or activation field distribution relative to the nerve, which may help minimize discomfort to patient 14 that results from the delivery of electrical stimulation therapy. An electrical field may define the volume of tissue that is affected when the electrodes 19, 20, 29 are activated. An activation field represents the neurons that will be activated by the electrical field in the neural tissue proximate to the activated electrodes.

The illustrated numbers and configurations of leads 18, 20, and 28 and electrodes carried by leads 18, 20, and 28 are merely exemplary. Other configurations, e.g., numbers and positions of leads and electrodes are also contemplated. For example, in other implementations, IMD 16 may be coupled to additional leads or lead segments having one or more electrodes positioned at different locations proximate the spinal cord or in the pelvic region of patient 14. The additional leads may be used for delivering different stimulation therapies to respective stimulation sites within patient 14 or for monitoring at least one physiological parameter of patient 14.

In accordance with some examples of the disclosure, IMD 16 delivers stimulation therapy periodically over an extended period of time, e.g., chronic stimulation, to at least one of a spinal nerve, a sacral nerve, a pudendal nerve, dorsal genital nerve, a tibial nerve, an inferior rectal nerve, a perineal nerve to provide an inhibitory physiogical response related to voiding of patient 14. In some examples, the inhibitory physiological response includes a reduction in bladder contraction frequency. In particular, IMD 16 may deliver stimulation therapy via at least one of electrodes 29 according to a therapy program for a first time period. The therapy program may define various parameters of the stimulation signal and electrode configuration which result in a predetermined stimulation intensity being delivered to the targeted nerve. In some examples, the therapy program defines parameters for at least one of a current amplitude of the stimulation signal, a voltage amplitude of the stimulation signal, a frequency or pulse rate of the stimulation signal, the shape of the stimulation signal, a duty cycle of the stimulation signal, a pulse width of the stimulation signal, or the combination of electrodes 29 and respective polarities of the subset of electrodes 29 used to deliver the stimulation signal. Together, these stimulation parameter values define the stimulation intensity (also referred to herein as a stimulation intensity level).

The therapy program defines a stimulation intensity which elicits a first inhibitory physiological response related to voiding of patient 14 during the first time period, while IMD 16 delivers the stimulation therapy. In some examples, the stimulation therapy elicits substantially no or no inhibitory physiological response related to voiding of patient 14 during the first time period. In other words, the physiological response of patient 14 during the first time period may be substantially unchanged or unchanged from the physiological response of patient 14 prior to IMD 16 delivering any stimulation therapy 16. In some examples, the physiological response comprises a contraction frequency of bladder 12. Accordingly, in some cases, a contraction frequency of bladder 12 is substantially the same (e.g., exactly the same) prior to stimulation therapy and during the first time period. In other examples, the contraction frequency of bladder 12 is reduced during the first time period compared to the contraction frequency of bladder 12 prior to delivery of stimulation to patient 14 by IMD 16.

The stimulation therapy delivered by IMD 16 elicits a second inhibitory physiological response of patient 14 during a second time period immediately following the first time period, during which the IMD 16 does not deliver stimulation therapy to patient 14. The second inhibitory physiological response may also be related to voiding and, for at least a portion of the second time period, may be greater than the first inhibitory physiological response. For example, the contraction frequency of bladder 12 may be lower for at least a portion of the second time period compared to the bladder contraction frequency during the first time period. In this way, the stimulation therapy delivered by IMD 16 during the first time period produces a post-stimulation inhibitory effect that extends beyond the first time period.

In some examples, the first and second time periods may have durations on the order of minutes. For example, the first time period, during which IMD 16 delivers stimulation therapy, may be between about 5 minutes and about 20 minutes. Similarly, the second time period, during which IMD 16 ceases to deliver stimulation therapy, may be between about 5 minutes and about 30 minutes. In some examples, the relative lengths of the first and second time periods may be selected to provide advantageous battery life to IMD 16 compared to an IMD 16 that delivers stimulation therapy substantially continuously (e.g., continuously).

Additionally or alternatively, it is believed that a stimulation pattern as described herein may reduce neuron habituation or other forms of patient adaptation to the stimulation therapy and extend an effective lifetime of the stimulation therapy (e.g., the time for which the stimulation therapy is efficacious in reducing bladder contraction frequency). It has been found that patient 14 may adapt to stimulation delivered by IMD 16 over time, such that a certain level of electrical stimulation provided to a tissue site in patient 16 may be less effective over time. This phenomenon may be referred to as "adaptation." As a result, any beneficial effects to patient 16 from the electrical stimulation may decrease over time. While the electrical stimulation levels (e.g., amplitude of the electrical stimulation signal) may be increased to overcome such adaptation, the increase in stimulation levels may consume more power, and may eventually reach undesirable levels of stimulation.

In some examples, the therapy program with which IMD 16 generates and delivers therapy to patient 14 may define a stimulation intensity which is less than a threshold stimulation intensity. As discussed above, the threshold stimulation intensity may be a physiological intensity threshold, which may be defined as approximately the lowest stimulation intensity at which an acute, physiologically significant response of patient 14 is first observed when increasing the stimulation intensity from a low intensity to a higher intensity. Stated another way, the threshold intensity may be defined as approximately the lowest stimulation intensity that elicits an acute, physiologically significant response of patient 14. In other examples, the threshold stimulation intensity may be a therapeutic intensity threshold, in that the stimulation is insufficient to cause a desired therapeutic effect during delivery of stimulation (e.g., during the first time period). However, the stimulation is sufficient to cause the desired therapeutic effect after the stimulation is terminated (e.g., during the second time period).

In some examples, once the threshold intensity is determined for patient 14, the stimulation parameter values may be changed such that the therapy program defines a stimulation intensity that is between about 50% and about 100% of the threshold intensity. The stimulation intensity may be changed by adjusting at least one of the stimulation parameters, such as, for example, a current amplitude of the stimulation signal, a voltage amplitude of the stimulation signal, a frequency of the stimulation signal, a pulse rate of the stimulation signal, a pulse width of the stimulation signal, the shape of the stimulation signal, the duty cycle of the stimulation signal, or the combination of electrodes 29. For example, the current and/or voltage amplitude of the stimulation signal may be reduced to reduce an intensity of the stimulation signal. IMD 16 may generate and deliver the stimulation signal as substantially continuous waveforms or as a series of pulses. As discussed in further detail below, this technique can be used to generate a therapy program that defines a first and/or second stimulation intensity.

In some examples, IMD 16 may deliver the stimulation therapy in an open loop manner, in which the first and second time periods alternate periodically to produce a therapy cycle. In some examples, each of the first time periods may be of substantially equal duration. Similarly, in some example, each of the second time periods may be of substantially equal duration. Furthermore, the first and second time periods can be of substantially equal duration. In the present disclosure, "substantially equal" can be, for example, equal or almost equal.

In some implementations, IMD 16 may deliver the stimulation therapy in a closed loop manner. For example, IMD 16 may sense contractions of bladder 12 during a time period prior to delivery of the stimulation therapy to establish a baseline contraction frequency of bladder 12 or the baseline contraction frequency may be stored in a memory of IMD 16 or another device (e.g., programmer 24). IMD 16 may sense contractions of bladder 12 via one or more means, such as, for example, electrodes 19 or 21, or sensor 22. IMD 16 may detect contractions of bladder 12 based on, for example, bladder impedance, bladder pressure, pudendal or sacral afferent nerve signals, a urinary sphincter EMG, or any combination thereof. IMD 16 then may utilize the sensed contractions of bladder 12 to determine a baseline contraction frequency of bladder 12, e.g., as a number of contractions of bladder 12 per unit time. The baseline contraction frequency of bladder 12 may represent the patient state when no therapeutic effects from delivery of stimulation by IMD 16 are present. In some cases, however, patient 14 may also receive other types of therapy for managing bladder dysfunction, such as a pharmaceutical agent. The baseline contraction frequency of bladder 12 may represent the patient state when patient 14 is under the influence of the pharmaceutical agent.

After determining a baseline contraction frequency, IMD 16 may then sense via electrodes 19 or 21 or sensor 22 a contraction frequency of bladder 12 during the second time period, after the first time period during which IMD 16 delivers stimulation therapy to patient 14. In some examples, IMD 16 may sense a contraction frequency of bladder 12 periodically throughout the second time period, e.g., once per minute within the second time period. IMD 16 may compare the contraction frequency of bladder 12 during the second time period to the baseline contraction frequency or a threshold frequency that is based on the baseline contraction frequency. The threshold frequency may be less than the baseline contraction frequency. In some examples, when the contraction frequency sensed during the second time period is within a certain value of the baseline contraction frequency or is above the threshold frequency, IMD 16 may initiate delivery of the stimulation therapy, e.g., restart the first time period.

In some examples, the therapy described above comprises a first stimulation therapy delivered by IMD 16, and IMD 16 also delivers a second stimulation therapy. For example, IMD 16 may deliver the first stimulation therapy chronically, e.g., non-temporarily, as a periodic repetition of first time periods during which IMD 16 delivers the first stimulation therapy and second time periods during which IMD 16 does not deliver the first stimulation therapy.

IMD 16 may automatically deliver the second stimulation therapy during at least one of the plurality of first time periods or the second time periods in response to a trigger event. In some examples, IMD 16 delivers the second stimulation therapy for a predetermined duration of time, referred to herein as a therapy period. In other examples, IMD 16 delivers the second stimulation therapy for a duration of time controlled by the patient. IMD 16 may deliver the first and second stimulation therapies at substantially the same time, during overlapping time slots, or in different time slots (e.g., during the second time periods), such that IMD 16 only delivers one type of stimulation therapy at a time. In examples in which IMD 16 delivers one type of stimulation therapy at a time, IMD 16 may deliver the first stimulation therapy, and, when triggered, deactivate delivery of the first stimulation therapy and activate delivery of the second stimulation therapy. After the second stimulation therapy period, IMD 16 may revert back to delivering the first stimulation therapy until another trigger event for activating the delivery of the second stimulation therapy is detected.

A trigger event for activating the delivery of the second stimulation therapy may be detected based on input from patient 14, sensor 22, or electrodes 19 and/or 21. As one example, IMD 16 may sense, via sensor 22, a bladder contraction that triggers IMD 16 to deliver the second stimulation therapy. As another example, patient 14 may use external programmer 24 to provide input that causes IMD 16 to deliver the second stimulation therapy. In this way, patient 14 may control delivery of the second stimulation therapy.

In some examples, IMD 16 may deliver the first stimulation therapy and a second stimulation therapy to patient 14 to generate different physiological responses. For example, the first stimulation therapy may generate an afferent response by patient 14, whereas the second stimulation therapy generates an efferent response. In some examples, IMD 16 delivers the first stimulation therapy to a spinal, sacral, pudendal, tibial, dorsal genital, inferior rectal, perineal or nerve of patient 14 to generate an afferent response that relaxes bladder 12, e.g., by reducing a contraction frequency of bladder 12.

In addition, in some examples, IMD 16 delivers the second stimulation therapy to promote contraction of the internal urinary sphincter 13 and/or external urinary sphincter 11 or periurethral muscles (not shown). In some cases, it may be undesirable for the external urinary sphincter or periurethral muscles to always remain closed, e.g., during the delivery of the chronic, first stimulation therapy. However, sphincter closure may help prevent the involuntary leakage of urine from bladder 12. Thus, the short-term closure of sphincter 11 and/or 13 provided by the second stimulation therapy may help prevent the occurrence of involuntary voiding events during the occurrence of acute bladder contractions.

In some examples, IMD 16 generates and delivers a first stimulation therapy and a second stimulation therapy to patient 14 according to different sets of stimulation parameters (which may also be referred to herein as therapy programs). In other examples, IMD 16 may deliver the first stimulation therapy and a second stimulation therapy to patient 14 to generate similar or identical physiological responses. For example, IMD 16 may deliver the first stimulation therapy and the second stimulation therapy to patient 14 to reduce a contraction frequency of bladder 12. In some implementations, the second stimulation therapy may include stimulation therapy similar to the first stimulation therapy, e.g., stimulation therapy that includes delivery of stimulation at a first stimulation intensity for a first time period, during which the stimulation elicits a first inhibitory physiological response, and ceasing delivery of stimulation for a second time period immediately following the first time period, during which the stimulation elicits a second inhibitory physiological response that is greater than the first inhibitory physiological response.

In some examples, the second stimulation therapy may be delivered according to stimulation parameter values that result in the second stimulation therapy being more efficacious than the first stimulation therapy. For example, the second stimulation therapy may be delivered at a higher stimulation intensity, for a longer first time period, and/or with a shorter second time period, which may result in the second stimulation therapy being more efficacious than the first stimulation therapy. As described above, the stimulation intensity may be affected by, for example, a current amplitude of the stimulation signal, a voltage amplitude of the stimulation signal, a frequency of the stimulation signal, a pulse rate of the stimulation signal, a pulse width of the stimulation signal, the shape of the stimulation signal, the duty cycle of the stimulation signal, or the combination of electrodes 29. As described above, when used with reference to the first and second stimulation therapies, the term "more efficacious" may refer to a more immediate inhibitory physiological effect, a greater inhibitory effect, or both.

As another example, IMD 16 may deliver the second stimulation therapy according to stimulation parameter values that produce a greater inhibitory physiological effect. For example, when the inhibitory physiological effect includes a reduction in bladder contraction frequency, the second stimulation therapy may reduce the bladder contraction frequency to a lower value than the first stimulation therapy.

In some examples in which IMD 16 delivers first and second stimulation therapies, IMD 16 delivers both the first and second stimulation therapies to patient 14 via electrodes 29 on lead 28. The target therapy site for the first and second stimulation therapies is the same in some examples, such as the same or different fibers of the same nerve. In other examples, the target stimulation site for the first and second stimulation therapies is different. For example, IMD 16 may deliver the first stimulation therapy to a spinal nerve of patient 14 to reduce contraction frequency of bladder 12 and deliver the second stimulation therapy to a hypogastric nerve to contract the internal urinary sphincter 11 and external urinary sphincter 13 or periurethral muscles, a pudendal nerve, a dorsal penile nerve in a male patient or a dorsal clitoral nerve in a female patient to contract the external urinary sphincter 13, periurethral muscles, the internal urinary sphincter 11, or any combination thereof.

In some examples, IMD 16 controls the delivery of the second electrical stimulation therapy based on input received from patient 14 or sensor 22, which generates a signal indicative of a parameter of patient 14 relating to bladder dysfunction, e.g., relating to a bladder condition or urinary incontinence, or fecal incontinence. As one example, IMD 16 may deliver the second stimulation therapy in response to detecting bladder contraction based on bladder impedance, bladder pressure, pudendal or sacral afferent nerve signals, a urinary sphincter EMG, or any combination thereof. As another example, IMD 16 may deliver the second stimulation therapy in response to detecting a patient activity level or patient posture state, with a sensor, which is indicative of an increased probability of an occurrence of an involuntary voiding event.

In some examples, IMD 16 may deliver the second stimulation therapy in response to receiving patient input. In this way, patient 14 may use external programmer 24 to trigger IMD 16 to deliver the second stimulation therapy. Patient 14 may initiate the delivery of the second stimulation therapy for many reasons. In some cases, patient 14 may be afflicted with urgency or urge incontinence, and upon perceiving an urge to void, patient 14 may provide input that causes IMD 16 to deliver the second stimulation therapy. In this way, therapy system 10 may provide patient 14 with direct control of the bladder dysfunction therapy.

In some examples, IMD 16 may deliver the second stimulation therapy to generate the second physiological response when contraction of bladder 12 exceeding a particular threshold is detected. In some implementations, IMD 16 determines an impedance through bladder 12, which varies as a function of the contraction of bladder 12, via electrodes 19 and 21 on leads 18 and 20, respectively. In the example shown in FIG. 1, IMD 16 may determine impedance of bladder 12 using a four-wire (or Kelvin) measurement technique. In other examples, IMD 16 may measure bladder impedance using a two-wire sensing arrangement. In either case, IMD 16 may transmit an electrical measurement signal, such as a current, through bladder 12 via leads 18 and 20, and determine impedance of bladder 12 based on the transmitted electrical signal. Such an impedance measurement may be utilized to determine response of contractions of bladder 12 to stimulation therapy, to determine a fullness of bladder 12, or the like.

In the example four-wire arrangement shown in FIG. 1, electrodes 19A and 21A and electrodes 19B and 21B, may be located substantially opposite each other relative to the center of bladder 12. For example electrodes 19A and 21A may be placed on opposing sides of bladder 12, either anterior and posterior or left and right. In FIG. 1, electrodes 19 and 21 are shown placed proximate to an exterior surface of the wall of bladder 12. In some examples, electrodes 18 and 21 may be sutured or otherwise affixed to the bladder wall. In other examples, electrodes 19 and 21 may be implanted within the bladder wall. To measure the impedance of bladder 12, IMD 16 may source an electrical signal, such as current, to electrode 19A via lead 18, while electrode 21A via lead 20 sinks the electrical signal. IMD 16 may then determine the voltage between electrode 19B and electrode 21B via leads 18 and 20, respectively. IMD 16 determines the impedance of bladder 12 using a known value of the electrical signal sourced the determined voltage.

In the example of FIG. 1, IMD 16 also includes a sensor 22 for detecting changes in the contraction of bladder 12. Sensor 22 may include, for example, a pressure sensor for detecting changes in bladder pressure, electrodes for sensing pudendal or sacral afferent nerve signals, electrodes for sensing urinary sphincter EMG signals (or anal sphincter EMG signals in examples in which therapy system 10 provides therapy to manage fecal urgency or fecal incontinence), or any combination thereof. In examples in which sensor 22 is a pressure sensor, the pressure sensor may be a remote sensor that wirelessly transmits signals to IMD 16 or may be carried on one of leads 18, 20, or 28 or an additional lead coupled to IMD 16. In some examples, IMD 16 may determine whether a contraction frequency of bladder 12 has occurred based on a signal generated by sensor 22. In examples in which sensor 22 includes one or more electrodes for sensing afferent nerve signals, the sense electrodes may be carried on one of leads 18, 20, or 28 or an additional lead coupled to IMD 16. In examples in which sensor 22 includes one or more sense electrodes for generating a urinary sphincter EMG, the sense electrodes may be carried on one of leads 18, 20, or 28 or additional leads coupled to IMD 16. In any case, in some examples IMD 16 controls the timing of the delivery of the first or second stimulation therapies based on input received from sensor 22.

In some examples in which IMD 16 delivers a first stimulation therapy and a second stimulation therapy, sensor 22 may comprise a patient motion sensor that generates a signal indicative of patient activity level or posture state. In some examples, IMD 16 controls the delivery of the second stimulation therapy to patient 14 upon detecting a patient activity level exceeding a particular threshold based on the signal from the motion sensor. The patient activity level that is greater than or equal to a threshold (which may be stored in a memory of IMD 16) may indicate that there is an increase in the probability that an incontinence event will occur, and, therefore, the second stimulation therapy may be desirable. In this way, the second stimulation therapy provided by IMD 16 may be useful for reacting to the circumstances that may affect patient incontinence and provide an additional layer of therapy to help prevent the occurrence of an involuntary voiding event.

In other examples in which IMD 16 delivers a first stimulation therapy and a second stimulation therapy, IMD 16 controls the delivery of the second stimulation therapy to patient 14 upon detecting a posture state associated with a high probability of an occurrence of an incontinence event based on the signal from the motion sensor. For example, patient 14 may be more prone to an incontinence event when patient 14 is in an upright posture state compared to a lying down posture state. IMD 16 may, for example, store a plurality of motion sensor signals and associate the signals with particular patient posture states using any suitable technique. IMD 16 may flag some of the posture states as being posture states for which additional therapy (e.g., delivery of the second stimulation therapy) to help prevent the occurrence of an incontinence event is desirable.

System 10 may also include an external programmer 24, as shown in FIG. 1. In some examples, programmer 24 may be a wearable communication device, with activation of the second stimulation therapy integrated into a key fob or a wrist watch, handheld computing device, computer workstation, or networked computing device. Programmer 24 may include a user interface that receives input from a user (e.g., patient 14, a patient caretaker or a clinician). In some examples, the user interface includes, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some examples, a display of programmer 24 may include a touch screen display, and a user may interact with programmer 24 via the display. It should be noted that the user may also interact with programmer 24 and/or ICD 16 remotely via a networked computing device.

A user, such as a physician, technician, surgeon, electrophysiologist, or other clinician, may also interact with programmer 24 or another separate programmer (not shown), such as a clinician programmer, to communicate with IMD 16. Such a user may interact with a programmer to retrieve physiological or diagnostic information from IMD 16, regardless of whether IMD 16 delivers only a single type of stimulation therapy or a first stimulation therapy and a second stimulation therapy. The user may also interact with a programmer to program IMD 16, e.g., select values for the stimulation parameter values with which IMD 16 generates and delivers stimulation and/or the other operational parameters of IMD 16. For example, the user may use a programmer to retrieve information from IMD 16 regarding the contraction of bladder 12 and/or voiding events. As another example, the user may use a programmer to retrieve information from IMD 16 regarding the performance or integrity of IMD 16 or other components of system 10, such as leads 18, 20, and 28, or a power source of IMD 16. In some examples, this information may be presented to the user as an alert if a system condition that may affect the efficacy of therapy is detected.

In some examples in which IMD 16 delivers a first stimulation therapy and a second stimulation therapy, patient 14 may interact with programmer 24 to control IMD 16 to deliver the second stimulation therapy, to manually abort the delivery of the second stimulation therapy by IMD 16 while IMD 16 is delivering the second stimulation therapy or is about to deliver the second stimulation therapy, or to inhibit the delivery of the second stimulation therapy by IMD 16, e.g., during voluntary voiding events. Patient 14 may, for example, use a keypad or touch screen of programmer 24 to cause IMD 16 to deliver the second stimulation therapy, such as when patient 14 senses that a leaking episode may be imminent. In this way, patient 14 may use programmer 24 to control the delivery of the second stimulation therapy "on demand," e.g., when patient 14 deems the second stimulation therapy desirable.

In some examples in which IMD 16 delivers the first stimulation therapy and the second stimulation therapy, patient 14 may interact with IMD 16 (e.g., via programmer 24 or directly via IMD 16) to control IMD 16 to deliver the second stimulation therapy, manually abort the delivery of the second stimulation therapy, or inhibit the delivery of the second stimulation therapy. In such examples, a motion sensor can be integrated into or on a housing of IMD 16, whereby the motion sensor generates a signal that is indicative of patient 14 tapping IMD 16 through the skin. The number, rate, or pattern of taps may be associated with the different programming capabilities, and IMD 16 may identify the tapping by patient 14 to determine when patient input is received. In this way, patient 14 may be able to directly control delivery of therapy in the event that programmer 24 is not within reach of patient 14.

In some examples, programmer 24 may provide a notification to patient 14 when the second stimulation therapy is being delivered or notify patient 14 of the prospective delivery of the second stimulation therapy to provide patient 14 with the opportunity to manually abort the second stimulation therapy. In such examples, programmer 24 may display a visible message, emit an audible alert signal or provide a somatosensory alert (e.g., by causing a housing of programmer 24 to vibrate). After generating the notification, programmer 24 may wait for input from patient 14 prior to delivering the second stimulation therapy. Patient 14 may enter input that either confirms delivery of the second stimulation therapy is permitted or desirable, or manually aborts the prospective delivery of the second stimulation therapy. In the event that no input is received within a particular range of time, programmer 24 may wirelessly transmit a signal that indicates the absence of patient input to IMD 16. IMD 16 may then elect to deliver or not to deliver the second stimulation therapy based on the programming of IMD 16.

Patient 14 may also interact with programmer 24 to inhibit the delivery of the second stimulation therapy during voluntary voiding events. That is, patient 14 may use programmer 24 to enter input that indicates the patient will be voiding voluntarily. When IMD 16 receives the input from programmer 24, IMD 16 may suspend delivery the second stimulation therapy for a predetermined period of time, e.g., two minutes, to allow the patient to voluntarily void.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

In examples in which IMD 16 delivers the first stimulation therapy and the second stimulation therapy, IMD 16 does not deliver the second stimulation therapy to patient 14 on a predetermined, scheduled basis, but as needed. For example, IMD 16 can deliver the second stimulation therapy to patient 14 when a particular patient parameter (e.g., a physiological parameter, activity level, or posture state) indicative of a high probability of an occurrence of an involuntary voiding event is detected or when input from patient 14 is received. In some examples, either IMD 16 or programmer 24 may track when IMD 16 delivers the second stimulation therapy to patient 14. Frequent delivery of the second stimulation therapy may be undesirable because, for example, muscle fatigue may result. Frequent delivery of the second stimulation therapy may indicate that, as another example, bladder 12 is full.

In some examples in which IMD 16 delivers the first and second stimulation therapy, programmer 24 may provide a notification to patient 14 when the second stimulation therapy is triggered too frequently. The notification may be triggered based on any suitable criteria, which may be determined by a clinician or automatically programmed into IMD 16 or programmer 24. For example, in the event that the second stimulation therapy is triggered five times within five minutes, programmer 24 may provide a notification to patient 14 indicating the same. This may allow patient 14 to proceed to a bathroom before a leaking episode occurs. The notification provided by programmer 24 may also direct patient 14 to voluntarily void.

Figure 2:
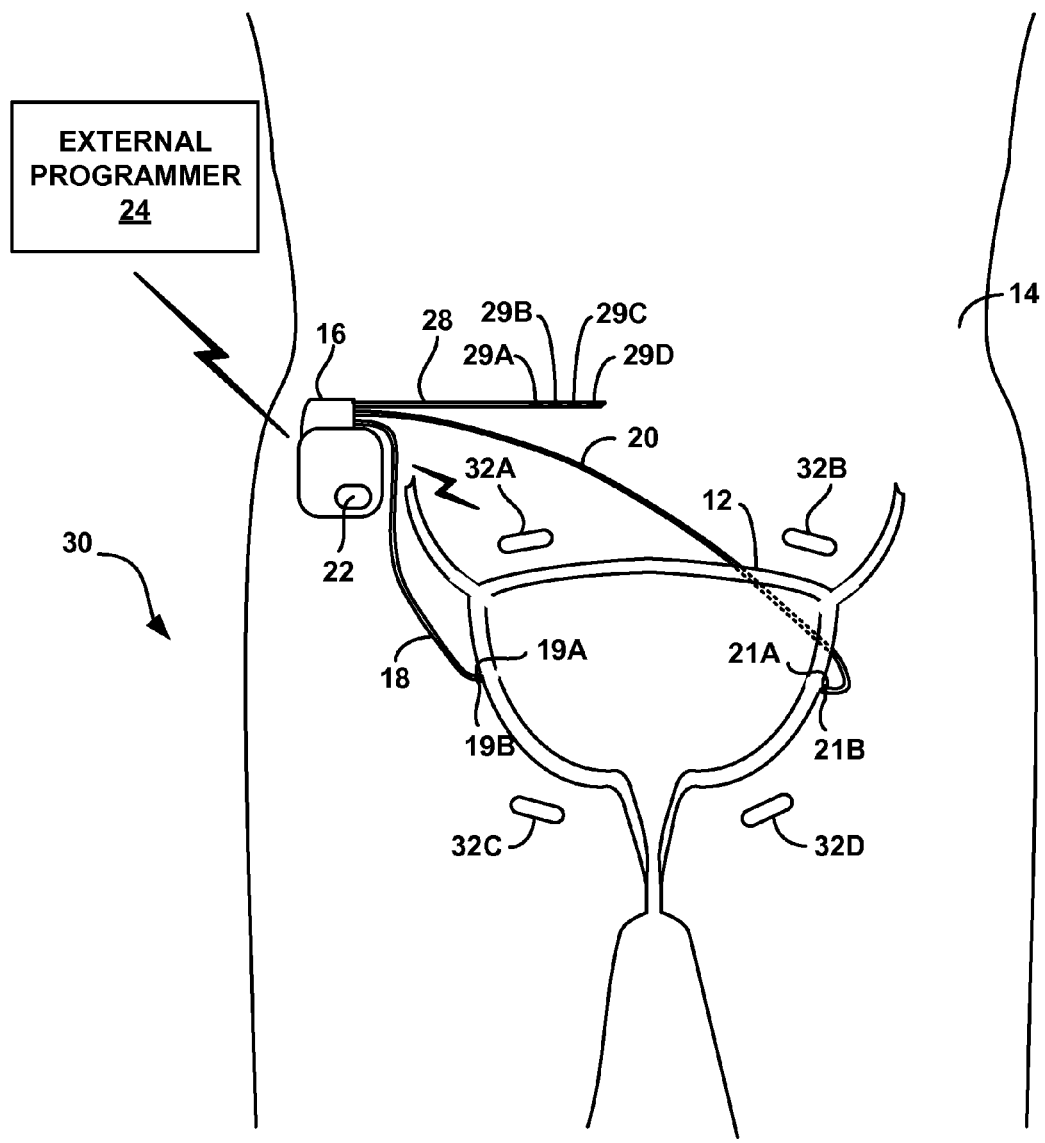
FIG. 2 is a conceptual diagram illustrating another example of a therapy system that delivers stimulation therapy to a patient to manage a bladder dysfunction.

FIG. 2 is conceptual diagram illustrating another example of a therapy system 30 that delivers stimulation therapy to generate an inhibitory physiological response in patient 14 to manage a bladder dysfunction of patient 14. As described above, the stimulation therapy may include delivery of stimulation during a first time period and cessation of delivery of stimulation during a second time period immediately following the first time period. The stimulation therapy may elicit an inhibitory physiological response during the second time period, and may or may not elicit an inhibitory physiological response during the first time period. Regardless, the inhibitory physiological response is greater for at least a portion of the second time period than during the first time period. In some examples, the inhibitory physiological response includes a reduction in bladder contraction frequency.

As described above, in some examples, the stimulation therapy is a first stimulation therapy that elicits a first physiological response to manage a bladder dysfunction of patient 14, and IMD 16 also delivers a second stimulation therapy to provide a second physiological response to manage the bladder dysfunction of patient 14. Therapy system 30 includes a distributed array of electrical stimulators, referred to herein as microstimulators 32A-32D (collectively referred to as "microstimulators 32"), in addition to IMD 16, leads 18, 20, and 28, sensor 22, and programmer 24. Microstimulators 32 are configured to generate and deliver electrical stimulation therapy to patient 14 vie one or more electrodes. Microstimulators 32 have a smaller size than IMD 16, and are typically leadless.

IMD 16 may deliver the stimulation therapy, or in some examples, one or both of the first or second electrical stimulation therapies, to patient 14 via microstimulators 32. For example, IMD 16 may communicate wirelessly with microstimulators 32 via wireless telemetry to control delivery of the first and, optionally, second stimulation therapies via microstimulators 32. In the example of FIG. 2, microstimulators 32 are implanted at different target stimulation sites. For example, microstimulators 32A and 32B may be positioned to stimulate a different set of nerves than microstimulators 32C and 324D. As an example, microstimulators 32A and 32B may target sacral nerves, while microstimulators 32C and 32D target the pudendal nerve. In other examples, microstimulators 32 may be implanted at various locations within the pelvic floor region, e.g., at different positions in proximity to the sacrum to target different nerves within the pelvic region. The illustrated number and configuration of microstimulators 32 is merely exemplary. Other configurations, e.g., number and position of microstimulators, are possible.

Systems 10 and 30 shown in FIGS. 1 and 2, respectively, are merely examples of delivers stimulation therapy to generate an inhibitory physiological response in patient 14 to manage a bladder dysfunction of patient 14. Systems with other configurations of leads, electrodes, and sensors are possible. Additionally, in other examples, a system may include more than one IMD. For example, a system may include an IMD coupled to one or more leads for delivering a first stimulation therapy and another IMD coupled to one or more leads for delivering a second stimulation therapy.

Figure 3:
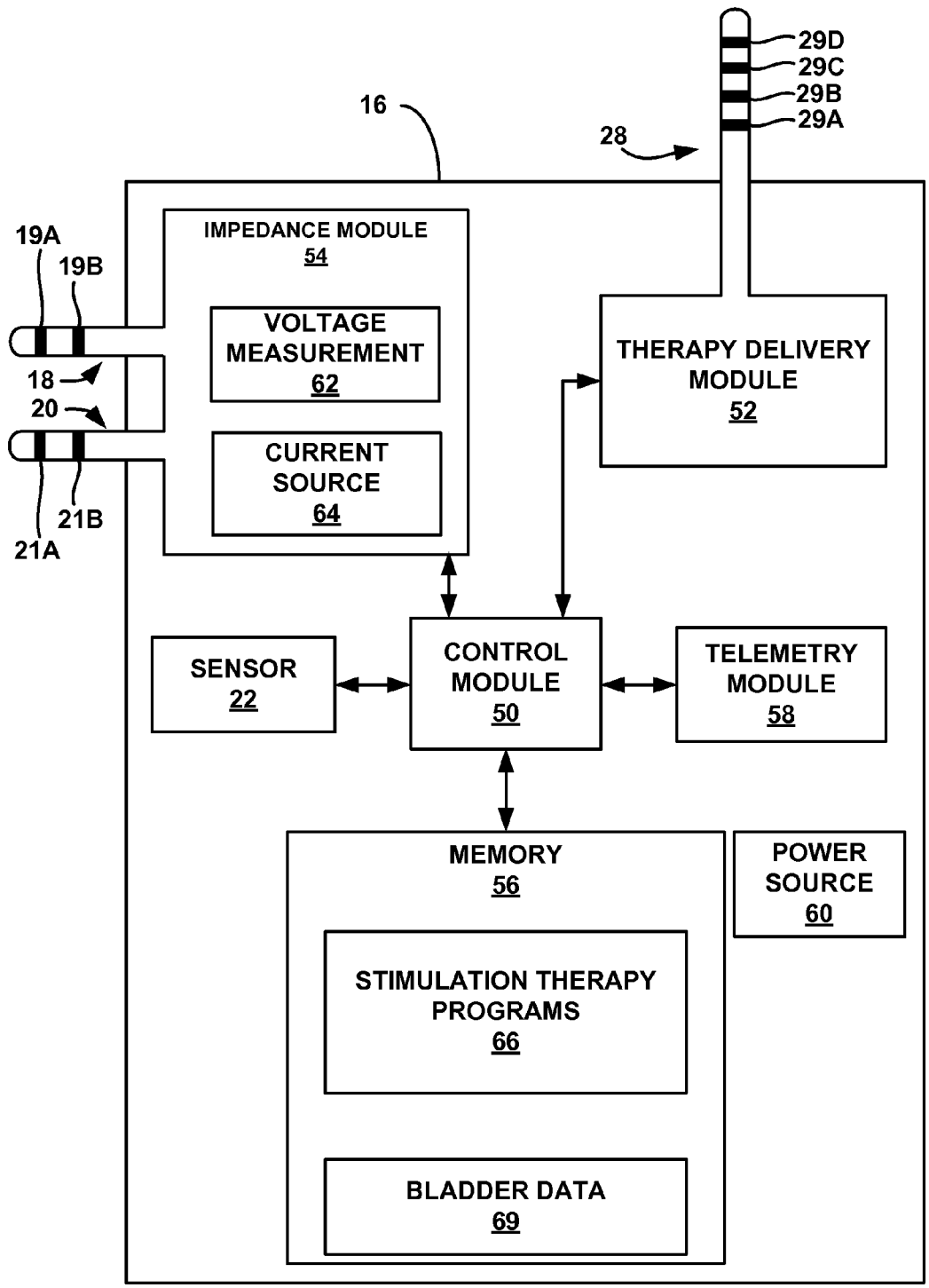
FIG. 3 is a block diagram illustrating an example configuration of an implantable medical device (IMD) which may be utilized in the systems shown in FIGS. 1 and 2.

FIG. 3 is a block diagram illustrating example components of IMD 16. In the example of FIG. 3, IMD 16 includes sensor 22, control module 50, therapy delivery module 52, impedance module 54, memory 56, telemetry module 58, and power source 60. In other examples, IMD 16 may include more or fewer components. For example, in some examples, such as examples in which IMD 16 may deliver only a first stimulation therapy and may operate in an open-loop manner, IMD 16 may not include sensor 22 and/or impedance module 54.

In general, IMD 16 comprises any suitable arrangement of hardware, alone or in combination with software and/or firmware, to perform the techniques attributed to IMD 16 and control module 50, therapy delivery module 52, impedance module 54, and telemetry module 58 of IMD 16. In various examples, IMD 16 may include one or more processors, such as one or more microprocessors, digital signal processors (DSPs), application specific integrated circuits (ASICs), field programmable gate arrays (FPGAs), or any other equivalent integrated or discrete logic circuitry, as well as any combinations of such components. IMD 16 also, in various examples, may include a memory 56, such as random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, or optical media comprising executable instructions for causing the one or more processors to perform the actions attributed to them. Moreover, although control module 50, therapy delivery module 52, impedance module 54, and telemetry module 58 are described as separate modules, in some examples, control module 50, therapy delivery module 52, impedance module 54, and telemetry module 58 are functionally integrated. In some examples, control module 50, therapy delivery module 52, impedance module 54, and telemetry module 58 correspond to individual hardware units, such as ASICs, DSPs, FPGAs, or other hardware units.

Memory 56 stores stimulation therapy programs 66 that specify stimulation parameter values for the stimulation therapy provided by IMD 16. In some examples, IMD 16 provides first and second stimulation therapies to patient 14, and the stimulation therapy programs 66 may include stimulation therapy programs for the first stimulation therapy and the second stimulation therapy. In some examples, memory 56 also stores bladder data 69, which control module 50 may use for controlling the timing of the delivery of the stimulation therapy (e.g., the single stimulation therapy or the first and/or second stimulation therapy). For example, bladder data 69 may include threshold values or baseline values for at least one of bladder impedance, bladder pressure, sacral or pudendal afferent nerve signals, bladder contraction frequency, or external urinary sphincter EMG templates. As described in further detail below, the threshold values and baseline values may indicate a particular event, such as a bladder contraction or a condition indicative of a voiding-related physiological condition (e.g., a patient state in which there is a relatively high likelihood of an involuntary voiding event).

Memory 56 may also store instructions for execution by control module 50, in addition to stimulation therapy programs 66 and bladder data 69. Information related to sensed bladder contractions, bladder impedance and/or posture of patient 14 may be recorded for long-term storage and retrieval by a user, or used by control module 50 for adjustment of stimulation parameters, such as amplitude, pulse width, and pulse rate. In some examples, memory 56 includes separate memories for storing instructions, electrical signal information, stimulation therapy programs, and bladder data.

Generally, therapy delivery module 52 generates and delivers stimulation therapy under the control of control module 50. In some examples, control module 50 controls therapy delivery module 52 by accessing memory 56 to selectively access and load at least one of stimulation therapy programs 66 to therapy delivery module 52. For example, in operation, control module 50 may access memory 56 to load one of stimulation therapy programs 66 to therapy delivery module 52.

By way of example, control module 50 may access memory 56 to load one of stimulation therapy programs 66 to therapy delivery module 52 for delivering the stimulation therapy to patient 14. A clinician or patient 14 may select a particular one of stimulation therapy programs 66 from a list using a programming device, such as programmer 24 or a clinician programmer. Control module 50 may receive the selection via telemetry module 58. Therapy delivery module 52 delivers the stimulation therapy to patient 14 according to the selected program for an extended period of time, such as hours, days, weeks, or until patient 14 or a clinician manually stops or changes the program. In some examples, the respective stimulation therapy programs 66 may define a schedule of first time periods ("on" periods) and second time periods ("off" periods), such that a stimulation signal is not continuously delivered to patient 14, but periodically delivered in accordance with predetermined parameters for the stimulation therapy. In other examples, control module 50 may determine the timing with which IMD 16 delivers stimulation to patient 14 according to different programs based on sensor input or patient input.

Therapy delivery module 52 delivers stimulation therapy, i.e., electrical stimulation, according to stimulation parameters. In some examples, therapy delivery module 52 delivers therapy in the form of electrical pulses. In such examples, relevant stimulation parameters may include a voltage amplitude, a current amplitude, a pulse rate, a pulse width, a duty cycle, or the combination of electrodes 29 therapy delivery module 52 uses to deliver the stimulation signal. In other examples, therapy delivery module 52 delivers electrical stimulation in the form of continuous waveforms. In such examples, relevant stimulation parameters may include a voltage amplitude, a current amplitude, a frequency, a shape of the stimulation signal, a duty cycle of the stimulation signal, or the combination of electrodes 29 therapy delivery module 52 uses to deliver the stimulation signal.

In some examples, the stimulation parameters for the stimulation programs 66 may be selected to relax bladder 12, e.g., to reduce a frequency of contractions of bladder 12. An example range of stimulation parameters for the stimulation therapy that are likely to be effective in treating bladder dysfunction, e.g., when applied to the spinal, sacral, pudendal, tibial, dorsal genital, inferior rectal, or perineal nerves, are as follows:

1. Frequency or pulse rate: between about 0.5 Hz and about 500 Hz, such as between about 5 Hz and about 250 Hz, between about 5 Hz and about 20 Hz, or about 10 Hz.

2. Amplitude: between about 0.001 volts and about 50 volts, such as between about 0.5 volts and about 20 volts, or between about 1 volt and about 10 volts, or between about 0.1 volts and about 2 volts. An amplitude between about 0.1 volts and about 2 volts may elicit a delayed inhibitory physiological response from patient 14 (e.g., an inhibitory physiological response that is observed within about two minutes to about five minutes after the initiation of the stimulation therapy).

3. Pulse Width: between about 10 microseconds (μs) and about 5000 μs, such as between about 100 μs and about 1000 μs, or between about 180 μs and about 450 μs.

Additionally, the stimulation parameters may include a duration of the first time period and a duration of the second time period. In some examples, the duration of the first time period is at least five minutes, such as between about five minutes and about 20 minutes, or about 10 minutes. In other words, in some examples, therapy delivery module 52 delivers stimulation to patient 14 via electrodes 29 for a duration of at least five minutes, such as between about five minutes and about 20 minutes or about 10 minutes.

In some examples the duration of the second period, during which therapy delivery module 52 does not deliver the stimulation therapy to patient 14, is at least five minutes, such as between five minutes and about 30 minutes or between about 10 minutes and about 20 minutes.

In some examples, the stimulation parameter values are selected from among those listed above such that the stimulation therapy elicits a first inhibitory physiological response related to voiding of patient 14 during the first time period and a second physiological response (e.g., an inhibition of a physiological function, such as bladder contractions, related to involuntary voiding) related to voiding of patient 14 during the second time period. In some examples, the stimulation parameters are selected such that the stimulation therapy elicits substantially no inhibitory physiological response related to voiding of patient 14 during the first time period. In other words, the physiological response of patient 14 may be substantially similar (e.g., identical or not physiologically significantly different) during the first time period and during a time period prior to the first time period during which therapy delivery module 52 delivers stimulation therapy to patient 14. As described above, in some examples, the first and second inhibitory physiological responses related to voiding include a reduction in contraction frequency of bladder 12 (FIG. 1).

In some examples, the stimulation therapy delivered to patient 14 by therapy delivery module 52 elicits a second physiological response related to voiding of patient 14 during the second time period which, for at least a portion of the second time period, is greater than the first physiological response of patient 14. For example, a contraction frequency of bladder 12 during at least a portion of the second time period may be lower than a contraction frequency of bladder 12 during the first time period. In this way, the stimulation therapy delivered by therapy delivery module 52 elicits a post-stimulation inhibitory effect that extends beyond the first time period, into the second time period.

In some examples, at least some of stimulation therapy programs 66 may define a stimulation intensity that is less than a threshold stimulation intensity. The threshold stimulation intensity may be defined as a physiological intensity threshold or a therapeutic intensity threshold, as described above.

In some implementations, control module 50 may determine the threshold intensity using the technique described above. For example, control module 50 can set stimulation parameters (e.g., a current amplitude, a voltage amplitude, a frequency or pulse rate, a pulse width, a shape, a duty cycle, and/or the combination of electrodes 29) to produce a relatively low stimulation intensity and control therapy delivery module 52 to deliver stimulation to patient 14 via electrodes 29 using these stimulation parameter values. If no physiological response is detected or observed, control module 50 may change one stimulation parameter automatically or in response to an input received from a user via programmer 24 and telemetry module 58, while the remaining parameters are kept approximately constant, and control module 50 may control therapy delivery module 52 to deliver stimulation at the new stimulation intensity. This may be repeated until a physiological response or a therapeutic response is detected or observed. The physiological response or therapeutic response may be observed by patient 12 or a clinician or may be detected by sensor 22 or electrodes 19, 21 coupled to IMD 16.

In some examples, once the threshold intensity is determined, control module 50 may define a therapy program, automatically or in response to an input received from a clinician via programmer 24 and telemetry module 58. The therapy program may be stored as one of stimulation therapy programs 66 in memory 56. In some examples, the therapy program may include stimulation parameters that define a stimulation intensity that is between about 50% and about 100% of the threshold intensity. In some implementations, the therapy program may include stimulation parameters that define a stimulation intensity that is about 75% of the threshold intensity. The stimulation intensity may be changed from the threshold intensity by adjusting a value of at least one of the stimulation parameters described above. For example, the current and/or voltage amplitude of the stimulation signal may be reduced to reduce an intensity of the stimulation signal.

In some examples, at least some of stimulation therapy programs 66 may define values for a set of stimulation parameters, including the durations of the first and second time periods, which cause therapy delivery module 52 to deliver stimulation therapy to patient 14 in an open loop manner. In such cases, therapy delivery module 52 delivers stimulation to patient 14 during each of the first time periods according to the same stimulation parameters. Additionally, the first and second time periods alternate and each first time period has the same duration and each second time period has the same duration. In some examples, therapy delivery module 52 continues to deliver stimulation therapy to patient 14 according to these stimulation parameters until receiving an instruction from control module 50 to interrupt therapy delivery. In some examples, control module 50 may issue such an instruction to therapy delivery module 52 in response to receiving an input for a user, such as a clinician, via telemetry module 58.

In some examples, at least one of stimulation therapy programs 66 defines stimulation parameters that cause therapy delivery module 52 to deliver stimulation therapy to patient 14 in a closed loop manner. In closed loop stimulation therapy, control module 50 or therapy delivery module 52 may deliver stimulation therapy to patient based on at least one feedback, e.g., a signal representative of a physiological response of patient 14 sensed by at least one of sensor 22, electrode 19, or electrode 21. For example, control module 50 or therapy delivery module 52 may control delivery of stimulation therapy by therapy delivery module 52 based on a contraction frequency of bladder 12. In some examples, the control of stimulation therapy delivery by control module 50 or therapy delivery module 52 may include controlling a duration of the second time period during which therapy delivery module 52 does not deliver stimulation therapy to patient 14.

To facilitate delivery of stimulation in a closed loop manner, the at least one of stimulation therapy programs 66 may include a baseline contraction frequency or a threshold contraction frequency. The baseline contraction frequency may be contraction frequency of bladder 12 at a time prior to delivery of stimulation therapy by therapy delivery module 52. For example, the baseline contraction frequency of bladder 12 may be sensed and determined by control module 50 after implantation of IMD 16 in patient 14, but before therapy delivery module 52 delivers any stimulation therapy to patient 14. In some examples, the baseline contraction frequency of bladder 12 may represent the patient state when no therapeutic effects from delivery of stimulation by IMD 16 are present.

Control module 50 may determine the baseline contraction frequency of bladder 12 utilizing signals representative of physiological parameters received from at least one of sensor 22, electrodes 19 or electrodes 21. In some examples, control module 50 monitors impedance of bladder 12 to detect contraction of bladder 12 based on signals received from impedance module 54. For example, control module 50 may determine an impedance value based on signals received from impedance module 54 and compare the determined impedance value to a threshold impedance value stored in memory 56 as bladder data 69. When the determined impedance value is less than the threshold value stored in bladder data 69, control module 50 detects bladder contraction. In some implementations, control module 50 monitors impedance of bladder 12 for a predetermine duration of time to detect contractions of bladder 12, and determines the baseline contraction frequency of bladder 12 by determining a number of contractions of bladder 12 in the predetermined duration of time.

In the example illustrated in FIG. 3, impedance module 54 includes voltage measurement circuitry 62 and current source 64, and may include an oscillator (not shown) or the like for producing an alternating signal, as is known. In some examples, as described above with respect to FIG. 1, impedance module 54 may use a four-wire, or Kelvin, arrangement. As an example, control module 50 may periodically control current source 64 to, for example, source an electrical current signal through electrode 19A and sink the electrical current signal through electrode 21A. In some examples, for collection of impedance measurements, current source 64 may deliver electrical current signals that do not deliver stimulation therapy to bladder 12, e.g., sub-threshold signals, due to, for example, the amplitudes or widths of such signals and/or the timing of delivery of such signals. Impedance module 54 may also include a switching module (not shown) for selectively coupling electrodes 19A, 19B, 21A, and 21B to current source 64 and voltage measurement circuitry 62. Voltage measurement circuitry 62 may measure the voltage between electrodes 19B and 21B. Voltage measurement circuitry 62 may include sample and hold circuitry or other suitable circuitry for measuring voltage amplitudes. Control module 50 determines an impedance value from the measure voltage values received from voltage measurement circuitry 52.

In other examples, control module 50 may monitor signals received from sensor 22 to detect contraction of bladder 12 and determine the baseline contraction frequency. In some examples, sensor 22 may be a pressure sensor for detecting changes in pressure of bladder 12, which control module 50 may correlate to contractions of bladder 12. Control module 50 may determine a pressure value based on signals received from sensor 22 and compare the determined pressure value to a threshold value stored in bladder data 69 to determine whether the signal is indicative of a contraction of bladder 12. In some implementations, control module 50 monitors pressure of bladder 12 to detect contractions of bladder 12 for a predetermined duration of time, and determines a contraction frequency of bladder 12 by calculating a number of contractions of bladder 12 in the predetermined time period.

In some examples, control module 50 causes the baseline contraction frequency to be stored in bladder data 69, and utilizes the baseline contraction frequency when delivering stimulation therapy in a closed loop manner. In other examples, control module 50 may cause a threshold contraction frequency to be stored as bladder data 69 in memory 56, and may utilize the threshold contraction frequency when delivering stimulation therapy in a closed loop manner, e.g., to determine when to deliver stimulation therapy to patient 14 according to a particular therapy program. In some implementations, control module 50 may, automatically or under control of a user, determine the threshold contraction frequency based on a baseline contraction frequency. For example, control module 50 may determine the threshold contraction frequency as a predetermined percentage of the baseline contraction frequency or a percentage of the baseline contraction frequency input by a user via programmer 24. As one example, the threshold frequency may be between approximately 75% and approximately 100% of the baseline contraction frequency.

In some examples, the threshold contraction frequency may not be based on a baseline contraction frequency of patient 12, and may instead be based on clinical data collected from a plurality of patients. For example, the threshold contraction frequency may be determined based on an average bladder contraction frequency of a plurality of patients during a bladder filling time period, i.e., during a time period in which the plurality patients are not experiencing a voluntary or involuntary voiding event. In any case, the threshold contraction frequency may be stored in bladder data 69, and, in some examples, control module 50 may utilize the threshold contraction frequency when delivering stimulation therapy in a closed loop manner to patient 14.

In other examples, instead of utilizing a threshold contraction frequency or a baseline contraction frequency, control module 50 may control closed-loop delivery of stimulation therapy based on an EMG template. In some implementations, sensor 22 may include an EMG sensor, and control module 50 may generate an EMG from the received signals generated by sensor 22. Sensor 22 may be implanted proximate to a muscle which is active when bladder 12 is contracting, such as a detrusor muscle. Control module 50 may compare an EMG collected during the second time period to EMG templates stored as bladder data 69 to determine whether the contractions of bladder 12 indicate a return to a baseline contraction frequency or pattern. In some cases, control module 50 may generate the EMG template based on received signals generated by sensor 22 after implantation of IMD 16, but before therapy delivery module 52 delivers any stimulation therapy to patient 14.

Control module 52, then, may utilize at least one of a threshold contraction frequency, a baseline contraction frequency, or a template EMG to control therapy delivery module 52 to deliver stimulation therapy in a closed loop manner. For example, during at least the second time periods, control module 50 may monitor impedance of bladder 12 to detect contraction of bladder 12 based on signals received from impedance module 54. In some implementations, control module 50 substantially continuously monitors impedance of bladder 12, at least during the second time periods, to detect contraction of bladder 12, and determines a contraction frequency of bladder 12 by determining a number of contractions of bladder 12 in a specified time period.

In other examples, sensor 22 may be a pressure sensor and control module 50 may monitor signals received from sensor 22 during at least a portion of the second time period to detect contraction of bladder 12. In some examples, control module 50 substantially continuously monitors pressure of bladder 12, at least during the second time periods, to detect contraction of bladder 12, and determines a contraction frequency of bladder 12 by determining a number of contractions of bladder 12 in a specified time period.

After determining a contraction frequency of bladder 12, control module 50 may compare the determined contraction frequency of bladder 12 to the threshold contraction frequency stored in memory 56 as bladder data 69. When the determined contraction frequency is greater than or substantially equal to the threshold contraction frequency stored in bladder data 69, control module 50 controls therapy delivery module 52 to initiate delivery of stimulation therapy to patient 14. In other words, control module 50 may end the second time period and initiate the first time period based on the determined contraction frequency being greater than or equal to the threshold contraction frequency.

In other examples, control module 50 may compare the determined contraction frequency of bladder 12 and the baseline contraction frequency to determine a difference between the determined contraction frequency and the baseline contraction frequency. In some examples, when the difference is less than or equal to a specified value (e.g., a threshold difference value) control module 50 may cause therapy delivery module 52 to initiate delivery of stimulation therapy to patient 14. In other words, control module 50 may end the second time period and initiate the first time period based on the difference between the determined contraction frequency and the baseline contraction frequency.

In other examples, sensor 22 may include an EMG sensor, and control module 50 may generate an EMG from the received signals generated by sensor 22 (e.g., which may sense the muscle activity with one or more sensor positioned near the target muscle) and compare the EMG to an EMG template stored as bladder data 69 to determine whether the contractions of bladder 12 are indicative of a predetermined characteristic which causes control module 50 to control therapy delivery module 52 to initiate delivery of the stimulation therapy. For example, the predetermined characteristic may be a frequency of contractions of bladder, an amplitude of the signal (representative of intensity of contractions of bladder 12), or the like.

In some implementations, closed loop therapy may allow control module 50 and therapy delivery module 52 to deliver more efficacious therapy to patient 14 by timing the delivery of the stimulation to respond to a specific physiological state (e.g., a bladder contraction frequency level) of patient 14. For example, based on the determined contraction frequency of bladder 12, control module 50 may cause therapy delivery module 52 to initiate delivery of stimulation therapy to patient 14 prior to the end of the second time period specified in the selected one of stimulation therapy programs 66. In this manner, closed loop therapy may reduce or substantially eliminate an amount of time that a contraction frequency of bladder 12 is at a baseline level (e.g., a level substantially similar to the contraction frequency of bladder 12 prior to delivery of any stimulation therapy).

As discussed above, delivery of stimulation during the first time period may generate a delayed physiological response that helps prevent the occurrence of an involuntary voiding event, whereby the physiological response is more pronounced during at least a portion of the second time period that follows the first time period. Thus, by timing the delivery of the stimulation to occur prior to observation of the baseline bladder contraction frequency, control module 50 may help time therapy such that there is sufficient time for the first therapy to generate the desired physiological response. In some examples, the first time period during which the stimulation is delivered to patient 14 is selected to generate the desired physiological response (e.g., a particular percentage of bladder contraction frequency or a particular bladder contraction frequency value) during the second time period. The delivery of the stimulation by therapy module 52 may not generate an acute physiological response in patient 14 that may help reduce the possibility of an occurrence of an involuntary voiding event, but, rather, such physiological response may be observed after delivering the stimulation for some minimum period of time, which may be less than or equal to the first time period.

As described above, in some implementations, the stimulation therapy described above, in which stimulation is delivered during a first time period of at least five minutes and is not delivered during a second period immediately following the first time period comprises a first stimulation therapy and therapy delivery module 52 also delivers a second stimulation therapy. The second stimulation therapy may provide a more acute physiological response that helps minimize the likelihood of an occurrence of an involuntary voiding event. The acute response may be observed in a shorter amount of time compared to the physiological response elicited from the delivery of the first stimulation therapy. In some examples in which therapy delivery module 52 delivers a first stimulation therapy and second stimulation therapy to patient 14, control module 50 may, when triggered, access memory 56 to load one of the stimulation therapy programs 66 to therapy delivery module 52, which therapy delivery module 52 utilizes to deliver the second stimulation therapy. Consistent with the techniques described in this disclosure, control module 50 may load one of stimulation therapy programs 66 to therapy delivery module 52 for delivery of the second stimulation therapy based on input received from impedance module 54, sensor 22, or an indication of input from patient 14 received from another device and transmitted to IMD 16 via telemetry module 58.

By way of example, control module 50 may access memory 56 to load one of stimulation therapy programs 66 to therapy module 52 for delivering the first stimulation therapy to patient 14. A clinician or patient 14 may select a particular one of stimulation therapy programs 66 from a list using a programming device, such as programmer 24 or a clinician programmer. Control module 50 may receive the selection via telemetry module 58. Therapy delivery module 52 delivers the first stimulation therapy to patient 14 according to the selected program for an extended period of time, such as hours, days, weeks, or until patient 14 or a clinician manually stops or changes the program.

Upon detecting a condition in which the second stimulation therapy is desirable to help prevent the occurrence of an incontinence event, such as in response to detecting bladder contractions or receiving patient input, control module 50 accesses memory 56 to load one of stimulation therapy programs 66 to therapy delivery module 52. Therapy delivery module 52 delivers the second stimulation therapy according to the selected one of stimulation therapy programs 66. In some examples, therapy module 52 delivers the second stimulation therapy for a predetermined therapy period, the duration of which may be stored in memory 56. The therapy period may be, for example, approximately 10 seconds to approximately 60 seconds, although other therapy periods are contemplated. That is, therapy delivery module 52 may deliver the second stimulation therapy according to the selected one of stimulation therapy programs 66 via bursts of stimulation for a duration of approximately 10 seconds to approximately 60 seconds.

In some examples, the therapy period, during which therapy delivery module 52 delivers the second stimulation therapy to patient 14, may be longer than approximately 60 seconds. For example, the second stimulation therapy may include a stimulation therapy similar to the first stimulation therapy, in which therapy delivery module 52 delivers stimulation to patient 14 during a first time period and ceases delivery of stimulation to patient 14 during a second time period immediately following the first time period. Therapy delivery module 52 may deliver the second stimulation therapy with stimulation parameters that result in a more efficacious therapy than the first stimulation therapy. For example, the therapy delivery module 52 may deliver the second stimulation therapy with a higher stimulation intensity, a longer first time period, and/or a shorter second time period than the first stimulation therapy. In such an example, the therapy period during which therapy delivery module 52 delivers the second stimulation therapy may be on the order of minutes or hours, and therapy delivery module 52 may cease delivering the first stimulation therapy during the time when therapy delivery module 52 delivers the second stimulation therapy. As described above, when used with reference to the first and second stimulation therapies, the term more efficacious may refer to a more immediate inhibitory physiological effect, a greater inhibitory effect, or both.

As another example, therapy delivery module 52 may deliver the second stimulation therapy according to stimulation parameter values that produce a greater inhibitory physiological effect. For example, when the inhibitory physiological effect includes a reduction in bladder contraction frequency, the second stimulation therapy may reduce the bladder contraction frequency to a lower value than the first stimulation therapy. As an example, the first stimulation therapy may reduce the bladder contraction frequency to between about 25% and about 50% of a baseline bladder contraction frequency (e.g., a frequency of bladder contractions when patient is not experiencing therapeutic effects of stimulation therapy), and the second stimulation therapy may reduce the bladder contraction frequency to less than about 25% of the baseline bladder contraction frequency.

In some examples, therapy delivery module 52 delivers the second stimulation therapy for a period of time controlled by patient 14. In such examples, patient 14 may interact with programmer 24 to control the delivery time. As an example, therapy delivery module 52 may deliver the second stimulation therapy as long as the patient presses a button on a keypad or touch screen of programmer 24. In operation, control module 50 receives the patient input via telemetry module 58 and controls therapy delivery module 52 to deliver therapy according to the received input.

In other examples, such as examples in which therapy delivery module 52 delivers the second stimulation therapy based on a sensed patient condition, therapy delivery module 52 delivers the second stimulation therapy until the condition is no longer detected. For example, therapy delivery module 52 may deliver the second stimulation therapy in response to detecting a bladder impedance less than or equal to a predetermined threshold and continue delivering the second stimulation therapy until the bladder impedance is greater than the predetermined threshold. In some examples, therapy delivery module 52 may pulse delivery of the second stimulation therapy. For example, therapy delivery module 52 may deliver the second stimulation therapy for an initial pulse of between about 10 and about 60 seconds, followed by a period of time in which therapy delivery module 52 does not delivery the second stimulation therapy. If control module 50 continues to sense the patient condition, therapy module 52 may deliver the second stimulation therapy for a second pulse of between about 10 and about 60 seconds. Such a pattern of pulsed second stimulation therapy may continue until control module 50 no longer senses the patient condition.

In some examples, therapy delivery module 52 delivers the second stimulation therapy at substantially the same time as the first stimulation therapy (e.g., during the one of the first time periods of the first stimulation therapy). In other examples, the second stimulation therapy may be delivered during one of the second time periods of the first stimulation therapy, e.g., when stimulation is not being delivered to patient 14 as part of the first stimulation therapy. The alternating therapies may be implemented if, for example, therapy delivery module 52 delivers the first and second stimulation therapies with a common set of electrodes. In the latter technique, when the second stimulation therapy has been delivered, therapy delivery module 52 may revert back to delivering the first stimulation therapy according to a first one of stimulation therapy programs 66 selected from memory 56.

The stimulation parameter values for the second stimulation therapy are generally different than those for the first stimulation therapy. Stimulation parameter values for the second stimulation therapy may be selected to maximize closure of one or more of internal urinary sphincter, external urinary sphincter, and periurethral muscles. Stimulation parameter values for the second stimulation therapy also or alternatively may be selected to more efficaciously reduce a contraction frequency of bladder 12. Stimulation parameter values for the second stimulation therapy may also be selected to minimize muscle fatigue. Muscle fatigue may occur when the force-generating ability of a muscle decreases as a result of the electrical stimulation.

An example range of stimulation pulse parameter values for the second stimulation therapy are as follows:

1. Frequency: between approximately 15 Hz to approximately 30 Hz to activate slow-twitch muscles to minimize muscle fatigue while providing some sphincter closure, and between approximately 30 Hz and approximately 66 Hz to activate fast-twitch muscles, which may maximize sphincter closure.

2. Amplitude: approximately 2-8 times rheobase (e.g., approximately 2-4 times rheobase) for the target nerve or muscle (e.g., the sphincter muscle), such as about 0.5 volts to about 50 volts, or about 0.5 volts to about 10 volts, or about 4 volts to about 8 volts. Rheobase is the minimal electric current of infinite duration that results in an action potential or muscle twitch.

3. Pulse Width: between about 10 microseconds (µs) and about 5,000 µs, such as between about 100 µs and approximately 1,000 µs.

As previously indicated, therapy delivery module 52 may deliver the second stimulation therapy for duration of time referred to as a therapy period. In some examples, the therapy period has a duration of about 10 seconds to about 60 seconds, although other therapy period durations, such as on the order of minutes or hours, are contemplated. In some examples, the therapy period duration is controlled by patient 14 through programmer 24, and may have a maximum period limit of about 3 minutes, although other maximum therapy periods for the second stimulation therapy are contemplated.

In some examples, the selected one of stimulation therapy programs 66 may define the simultaneous delivery of stimulation at multiple frequencies during the second stimulation therapy. As an example, a stored second stimulation therapy program 68 may define segmented electrodes to simultaneously deliver higher frequency (e.g., 66 Hz) stimulation to fascicles responsible for fast muscles, such as the Iliococcygeus muscle and the pubococcygeus muscle, and lower frequency stimulation (e.g., 30 Hz) to fascicles responsible for slow muscles, such as the soleus muscle.

In the example of FIG. 3, therapy delivery module 52 drives a single lead 28. Specifically, therapy delivery module 52 delivers electrical stimulation to tissue of patient 14 via selected electrodes 29A-29D carried by lead 28. A proximal end of lead 28 extends from the housing of IMD 16 and a distal end of lead 28 extends to a target therapy site, such as a spinal nerve (e.g., an S3 nerve), or a therapy site within the pelvic floor, such as tissue sites proximate a sacral nerve, a pudendal nerve, a tibial nerve, a dorsal genital nerve, an inferior rectal nerve, a perineal nerve, a hypogastric nerve, a urinary sphincter, or any combination thereof. In other examples, therapy delivery module 52 may deliver electrical stimulation with electrodes on more than one lead and each of the leads may carry one or more electrodes. The leads may be configured as an axial leads with ring electrodes and/or paddle leads with electrode pads arranged in a two-dimensional array. The electrodes may operate in a bipolar or multipolar configuration with other electrodes, or may operate in a unipolar configuration referenced to an electrode carried by the device housing or "can" of IMD 16. In yet other examples, such as system 30 shown in FIG. 2 that includes microstimulators 32, control module 50 may act as a "master" module that controls microstimulators to deliver stimulation at target therapy sites. In other examples, however, one of microstimulators 32 may act as a master module or microstimulators 32 may be self-controlled.

In some examples, control module 50 controls therapy module 52 to deliver the second stimulation therapy to patient 14 based on signals received from impedance module 54, sensor 22, or patient input received via telemetry module 58. For example, control module 50 may determine an impedance value based on signals received from impedance module 54 and compare the determined impedance value to a threshold impedance value stored in memory 56 as bladder data 69. When the determined impedance value is less than the threshold impedance value stored in bladder data 69, control module 50 detects bladder contraction of sufficient intensity to warrant delivery of the second stimulation therapy. Control module 50 then loads one of second stimulation therapy programs 68 to therapy module 52, and therapy module 52 generates and delivers the second stimulation therapy to patient 14 to generate a physiological response that helps prevent an incontinence event. As previously indicated, the physiological response generated by the delivery of the second stimulation therapy differs from the physiological response generated by the delivery of the first stimulation therapy to provide an additional layer of incontinence prevention.

As previously described, sensor 22 may comprise a pressure sensor for detecting changes in bladder pressure, electrodes for sensing pudendal or sacral afferent nerve signals, or electrodes for sensing external urinary sphincter EMG signals (or anal sphincter signals in examples in which IMD 16 provides fecal urgency or fecal incontinence therapy), or any combination thereof. Additionally or alternatively, sensor 22 may comprise a motion sensor, such as a two-axis accelerometer, three-axis accelerometer, one or more gyroscopes, pressure transducers, piezoelectric crystals, or other sensors that generate a signal that changes as patient activity level or posture state changes. Control module 50 may detect a patient condition indicative of a high probability of an incontinence event (e.g., bladder contraction or abnormal detrusor muscle activity) or other trigger events based on signals received from sensor 22 in addition to instead of impedance module 54. Sensor 22 may also be a motion sensor that is responsive to tapping (e.g., by patient 14) on skin superior to IMD 16 and, as previously described, control module 50 may control therapy module 52 to deliver second stimulation therapy, manually abort delivery of second stimulation therapy, or inhibit the delivery of second stimulation therapy, in response to detection of the patient tapping.

One type of bladder contraction detection algorithm indicates an occurrence of a bladder contraction for which delivery of the second stimulation therapy is desirable upon sensing of a signal that exhibits a certain characteristic, which may be a time domain characteristic (e.g., a mean, median, peak or lowest signal amplitude within a particular time period) or a frequency domain characteristic (e.g., an energy level in one or more frequency bands or a ratio of energy levels in different frequency bands). For example, the bladder contraction detection algorithm may indicate the occurrence of a bladder contraction for which delivery of the second stimulation therapy is desirable when the amplitude of the signal from sensor 22 meets a certain condition relative to a threshold (e.g., is greater than, equal to or less than the threshold). Another bladder contraction detection algorithm indicates the occurrence of a bladder contraction for which delivery of the second stimulation therapy is desirable if a sensed signal substantially correlates to a signal template, e.g., in terms of frequency, amplitude and/or spectral energy characteristics. Control module 50 may use known techniques to correlate a sensed signal with a template in order to detect the bladder contraction or detect the bladder contraction based on the frequency domain characteristics of a sensed signal. Other bladder contraction techniques may be used.

In examples in which sensor 22 includes a pressure sensor, control module 50 may determine a pressure value based on signals received from the pressure sensor and compare the determined pressure value to a threshold value stored in bladder data 69 to determine whether the contractions of bladder 12 are indicative of an imminent incontinence event. In examples in which sensor 22 includes an EMG sensor, control module 50 may generate an EMG from the received signals generated by sensor 22 (e.g., which may sense the muscle activity with one or more sensor positioned near the target muscle) and compare the EMG to templates stored as bladder data to determine whether the contractions of bladder 12 are indicative of an imminent incontinence event. Alternatively, control module 50 may compare previously collected EMGs to a current EMG to detect changes over time. The techniques for detecting bladder contractions may also be applied to detecting abnormal detrusor muscle activities.

In examples in which sensor 22 includes a motion sensor, control module 50 may determine a patient activity level or posture state based on a signal generated by sensor 22. For example, control module 50 may determine a patient activity level by sampling the signal from sensor 22 and determining a number of activity counts during a sample period, where a plurality of activity levels are associated with respective activity counts. In one example, control module 50 compares the signal generated by sensor 22 to one or more amplitude thresholds stored within memory 56, and identifies each threshold crossing as an activity count.

Control module 50 may determine a patient posture state based on a signal from sensor 22 using any suitable technique. In one example, a posture state may be defined as a three-dimensional space (e.g., a posture cone or toroid), and whenever a posture state parameter value, e.g., a vector from a three-axis accelerometer of sensor 22 resides within a predefined space, control module 50 indicates that patient 14 is in the posture state associated with the predefined space.

Memory 56 may associate patient posture states or activity levels with the second stimulation therapy, such that when control module 50 detects a posture state or activity level associated with the second stimulation therapy, control module 50 controls therapy delivery module 52 to generate and deliver the second stimulation therapy to patient 14. Certain posture states or activity levels may be associated with a higher incidence of incontinence events. For example, patient 14 may have less control of the pelvic floor muscles when occupying an upright posture state or when patient 14 is in a highly active state (e.g., as indicated by a stored activity count or a threshold activity signal value). Thus, detection of these activity levels or posture states may be triggers for the delivery of the second stimulation therapy.

The threshold values (also referred to as threshold levels) or templates (e.g., indicating a signal indicative of an imminent voiding event) stored in memory 56 as bladder data 69 may be determined using any suitable technique. In some examples, the threshold values may be determined during implantation of IMD 16 or during a trial period in a clinician's office following the implant procedure. For example, a clinician may record impedance values during involuntary voiding events and use the recorded impedance values or values calculated based on the recorded values as threshold values. These threshold values may be adapted over time based on user input, e.g., via external programmer 24. As an example, patient 14 may indicate, via programmer 24, when an involuntary voiding event takes place. When the patient input is received, control module 50 may determine an impedance value during the event or immediately prior to the event based in signals received from impedance module 54. A new threshold value may be determined using this impedance value. For example, the threshold value stored as bladder data 69 may be a running average of impedance values measured during involuntary voiding events.

In some examples, control module 50 may control therapy delivery module 52 to deliver the second stimulation therapy based on patient input received via telemetry module 58. Telemetry module 58 includes any suitable hardware, firmware, software or any combination thereof for communicating with another device, such as programmer 24 (FIG. 1). Under the control of control module 50, telemetry module 58 may receive downlink telemetry, e.g., patient input, from and send uplink telemetry, e.g., an alert, to programmer 24 with the aid of an antenna, which may be internal and/or external. Control module 50 may provide the data to be uplinked to programmer 24 and the control signals for the telemetry circuit within telemetry module 58, and receive data from telemetry module 58.

Generally, control module 50 controls telemetry module 58 to exchange information with medical device programmer 24 and/or another device external to IMD 16. Control module 50 may transmit operational information and receive stimulation programs or stimulation parameter adjustments via telemetry module 58. Also, in some examples, IMD 16 may communicate with other implanted devices, such as stimulators, control devices, or sensors, via telemetry module 58.

As previously described, in some examples, telemetry module 58 may receive an indication that patient 14 provided input indicative of an imminent voiding event or a desire for delivery of the second stimulation therapy, from programmer 24. Upon receiving the patient input via telemetry module 58, control module 50 may control therapy delivery module 52 to generate and deliver the second stimulation therapy for a predetermined amount of time or until a particular patient condition is detected, to manually abort the second stimulation therapy, or inhibit the second stimulation therapy during voluntary voiding. Control module 50 monitors patient input received via telemetry module 58 and takes appropriate action. For example, telemetry module 58 may receive input from programmer 24 that indicates a specified one of second stimulation therapy programs 68 should be selected for delivery of the second stimulation therapy program. Upon receiving the input, control module 50 loads the specified one of second stimulation therapy programs 68 to therapy module 52.

In an example in which telemetry module 58 receives patient input indicating a voluntary voiding event, control module 50 may suspend delivery of the second stimulation therapy for a pre-determined period of time, e.g., 2 minutes. In response to receiving the input, control module 50 may ignore signals indicative of the patient parameter, such as impedance signals received from impedance module 54. Control module 50 may ignore these signals for a predetermined period of time, such as approximately two minutes. After two minutes has elapse, control module 50 may continue monitoring patient 14 to detect trigger events.

Power source 60 delivers operating power to the components of IMD 16. Power source 60 may include a battery and a power generation circuit to produce the operating power. In some examples, the battery may be rechargeable to allow extended operation. Recharging may be accomplished through proximal inductive interaction between an external charger and an inductive charging coil within IMD 16. In other examples, an external inductive power supply may transcutaneously power IMD 16 whenever stimulation therapy is to occur.

Figure 4:
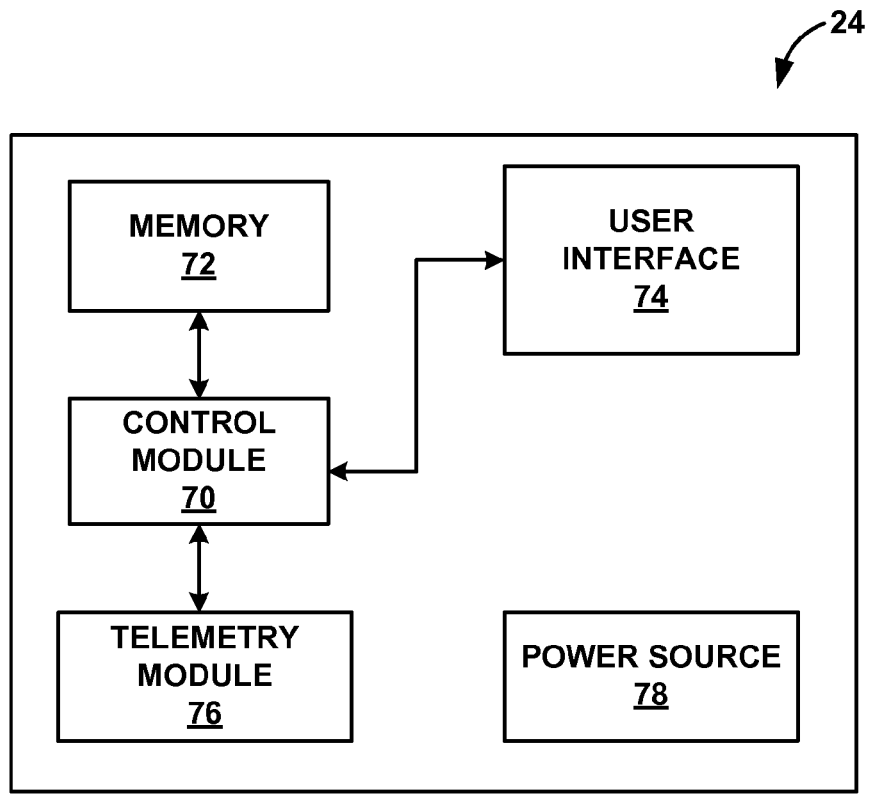
FIG. 4 is a block diagram illustrating an example configuration of an external programmer which may be utilized in the systems shown in FIGS. 1 and 2.

FIG. 4 is a block diagram illustrating example components of external programmer 24. While programmer 24 may generally be described as a hand-held computing device, the programmer may be a notebook computer, a cell phone, or a workstation, for example. As illustrated in FIG. 4, external programmer 24 may include a control module 70, memory 72, user interface 74, telemetry module 76, and power source 78. Memory 72 may store program instructions that, when executed by control module 70, cause control module 70 and external programmer 24 to provide the functionality ascribed to external programmer 24 throughout this disclosure.

In general, programmer 24 comprises any suitable arrangement of hardware, alone or in combination with software and/or firmware, to perform the techniques attributed to programmer 24, and control module 70, user interface 74, and telemetry module 76 of programmer 24. In various examples, programmer 24 may include one or more processors, such as one or more microprocessors, DSPs, ASICs, FPGAs, or any other equivalent integrated or discrete logic circuitry, as well as any combinations of such components. Programmer 24 also, in various examples, may include a memory 72, such as RAM, ROM, PROM, EPROM, EEPROM, flash memory, a hard disk, a CD-ROM, a floppy disk, a cassette, magnetic media, or optical media comprising executable instructions for causing the one or more processors to perform the actions attributed to them. Moreover, although control module 70 and telemetry module 76 are described as separate modules, in some examples, control module 70 and telemetry module 76 are functionally integrated. In some examples, control module 70 and telemetry module 76 and telemetry module 58 correspond to individual hardware units, such as ASICs, DSPs, FPGAs, or other hardware units.

Memory 72 may store program instructions that, when executed by control module 70, cause control module 70 and programmer 24 to provide the functionality ascribed to programmer 24 throughout this disclosure. In some examples, memory 72 may further include program information, i.e., therapy programs defining the first type of stimulation therapy and, optionally, therapy programs defining the second type of stimulation therapy, similar to those stored in memory 56 of IMD 16. The stimulation programs stored in memory 72 may be downloaded into memory 56 of IMD 16.

User interface 74 may include a button or keypad, lights, a speaker for voice commands, a display, such as a liquid crystal (LCD), light-emitting diode (LED), or cathode ray tube (CRT). In some examples the display may be a touch screen. As discussed in this disclosure, control module 70 may present and receive information relating to stimulation therapy via user interface 74. For example, control module 70 may receive patient input via user interface 74. The input may be, for example, in the form of pressing a button on a keypad or selecting an icon from a touch screen.

Control module 70 may also present information to the patient in the form of alerts related to delivery of the stimulation therapy to patient 14 or a caregiver, as will be described in more detail below, via user interface 74. Although not shown, programmer 24 may additionally or alternatively include a data or network interface to another computing device, to facilitate communication with the other device, and presentation of information relating to first and second stimulation therapies via the other device.

Telemetry module 76 supports wireless communication between IMD 16 and programmer 24 under the control of control module 70. Telemetry module 76 may also be configured to communicate with another computing device via wireless communication techniques, or direct communication through a wired connection. Telemetry module 76 may be substantially similar to telemetry module 58 of IMD 16, providing wireless communication via an RF or proximal inductive medium. In some examples, telemetry module 76 may include an antenna, which may take on a variety of forms, such as an internal or external antenna. An external antenna that is coupled to programmer 24 may correspond to a programming head that may be placed over IMD 16.

Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection.

IMD 16 and/or programmer 24 may control of the timing of the delivery of the stimulation therapy or, in some examples, the first and second stimulation therapies, that generate one or more physiological responses to manage bladder dysfunction. If external programmer 24 controls the stimulation, programmer 24 may transmit therapy programs for implementation by control module 50 to IMD 16 via telemetry module 76. A user (e.g., patient 14 or a clinician) may select the first and second stimulation therapy programs from a list provided via a display of user interface 74. In some cases, programmer 24 may transmit a signal to IMD 16 indicating that control module 50 should execute locally stored programs or therapy routines. In such a manner, control over the electrical stimulation may be distributed between IMD 16 and external programmer 24, or may reside in either one alone.

In one example in which IMD 16 delivers first and second stimulation therapies, patient 14 may control the second stimulation therapy delivered by IMD 16 via programmer 24. For example, patient 14 may initiate or terminate delivery of the second stimulation therapy by IMD 16 via user interface 74. In this way, patient 14 may use programmer 24 to deliver the second stimulation therapy "on demand," such as when patient 14 senses the onset of a leakage episode or undertakes an activity in which an additional measure of therapy to help prevent the occurrence of an involuntary voiding event is desirable.

In some examples in which IMD 16 delivers first and second stimulation therapies, patient 14 may indicate an intent to void via user interface 74, and control module 70 may implement a blanking interval through communication of the indication to IMD 16 via telemetry module 76. For example, control module 70 may transmit a command signal to IMD 16 that indicates control module 50 should temporarily suspend delivery of the second stimulation therapy. In some cases, this may permit voluntary voiding by patient 14. In some examples, the length of time for a voiding event may be determined by pressing and holding down a button of user interface 74 for the duration of a voiding event, pressing a button a first time to initiate voiding and a second time when voiding is complete, or based on a predetermined period of time following the indication of voluntary voiding provided by patient 14. In each case, programmer 24 causes IMD 16 to temporarily suspend the second stimulation therapy so that voluntary voiding is possible.

Power source 78 delivers operating power to the components of programmer 24. Power source 78 may include a battery and a power generation circuit to produce the operating power. In some examples, the battery may be rechargeable to allow extended operation.

FIGS. 5-9 are flow diagrams illustrating examples of techniques implemented by a therapy system, such as therapy system 10 (FIG. 1) to reduce the likelihood of incontinence events. While FIGS. 5-9 and other techniques described herein are described with respect to therapy system 10, in other examples, the techniques for delivering bladder dysfunction therapy may be implemented by other therapy systems, which may include different components or configurations than therapy system 10.

In some examples, therapy system 10 may deliver a single stimulation therapy that includes a plurality of first time periods, during which system 10 delivers stimulation at a first stimulation intensity, and second time periods, during which system 10 delivers stimulation at a second stimulation intensity that is less than the first stimulation intensity or does not deliver stimulation. In other examples, therapy system 10 may deliver a first, chronic stimulation therapy that includes the first and second time periods, and a second, acute stimulation therapy, which is triggered by a trigger event, such as a physiological event or a patient input. FIGS. 5-9 will be described with respect to FIGS. 1 and 3 for ease of description, although the techniques illustrated in FIGS. 5-9 can be implemented via other therapy systems. Additionally, the flow diagrams shown in FIGS. 5-9 include some of the same steps, which are like-numbered for ease of description.

Figure 5:
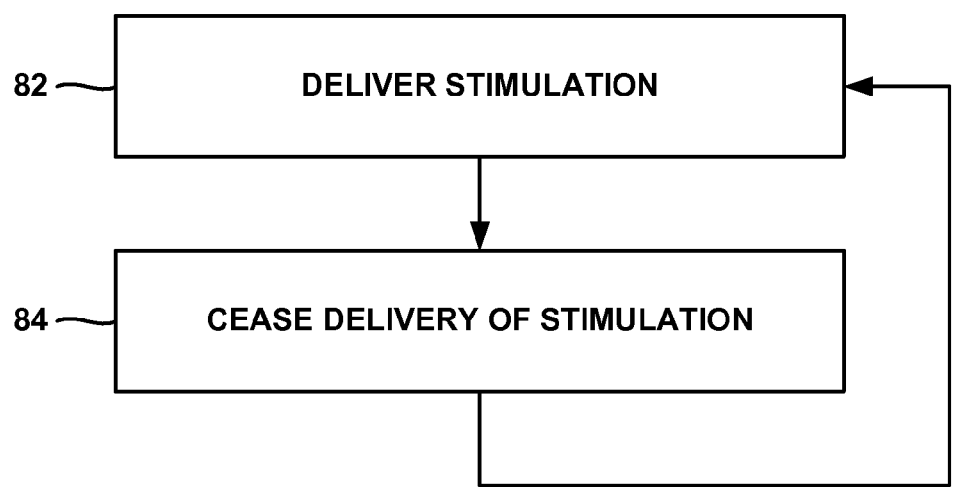
FIG. 5 is a flow diagram that illustrates an example technique for delivering stimulation therapy that includes a plurality of alternating first and second time periods to manage a bladder dysfunction.

FIG. 5 is a flow diagram that illustrates an example of a technique for delivering stimulation therapy that includes a plurality of alternating first and second time periods to manage bladder dysfunction. Under control of control module 50, therapy delivery module 52 of IMD 16 delivers stimulation therapy to patient 14 according to a therapy program (82). In some examples, control module 50 initiates the delivery of the first stimulation therapy by therapy delivery module 52 upon activation of chronic therapy delivery by the clinician via programmer 24. Therapy delivery module 52 delivers the stimulation therapy chronically, e.g., for an extended period of time, such as hours, days, weeks, or longer.

As described above, the stimulation therapy may include a first time period during which therapy delivery module 52 delivers stimulation to patient 14 according to a therapy program and a second time period during which therapy delivery module 52 does not deliver stimulation to patient 14 according to the therapy program (84). The first and second time periods generally alternate, such that the second time period may begin immediately upon the ending of the first time period. Similarly, the stimulation therapy continues with another first time period immediately upon the ending of the second time period. In this way, the first and second time periods may alternate periodically to define the stimulation therapy delivered by therapy delivery module 52.

Each of the first and second time periods may have a predetermined duration, which may be stored in the respective stimulation therapy programs 66 in memory 56 of IMD 16. In some examples, the duration of each of the first time periods is greater than about 5 minutes, such as between about 5 minutes and about 20 minutes, or about 10 minutes. In some examples, the duration of each of the second time periods is greater than about 5 minutes, such as between about 5 minutes and about 30 minutes, or between about 10 minutes and about 20 minutes. In some implementations, the durations of the first time periods and the second time periods are the same, which in other implementations, the durations of the first time periods and the second time periods are different.

The time periods may be selected based on various factors. For example, as discussed above, stimulation during the first time period may generate a delayed physiological response that helps prevent the occurrence of an involuntary voiding event, whereby the physiological response is more pronounced during the second time period that follows the first time period. The physiological response may not be generated until the first stimulation therapy is delivered to patient 14 for at least a minimum duration of time (e.g., at least about 5 minutes, such as between about 5 minutes and about 30 minutes or about 10 minutes). Thus, the first time period may be selected to be the time period sufficient to generate the desired physiological response (e.g., a particular percentage of bladder contraction frequency or a particular bladder contraction frequency value) during the second time period.

Upon the ending of the first time period, therapy delivery module 52 ceases delivering stimulation to patient 14 according to the therapy program, and in some cases, ceases delivery of all stimulation (84), for the duration of the second time period. Conversely, at the end of the second time period, therapy delivery module 52 initiates delivery of stimulation to patient 14 (82). Together, the first and second time periods define the stimulation therapy delivered to patient 14 by therapy delivery module 52.

During the first time periods, therapy delivery module 52 may deliver stimulation therapy that elicits either substantially no inhibitory physiological response related to voiding of patient 14 or first inhibitory physiological response related to voiding of patient 14. As described above, in some examples, the first and second inhibitory physiological responses related to voiding include a reduction in contraction frequency of bladder 12.

The stimulation therapy delivered to patient 14 by therapy delivery module 52 elicits a second physiological response related to voiding of patient 14 during the second time period which, for at least a portion of the second time period, is greater than the first physiological response of patient 14. For example, a contraction frequency of bladder 12 during at least a portion of the second time period, and, in some cases, the entire second time period, may be lower than a contraction frequency of bladder 12 during the first time period. In this way, the stimulation therapy delivered by therapy delivery module 52 elicits a post-stimulation inhibitory effect that extends beyond the first time period, into the second time period. Because the second physiological response may not be observed during the first time period, the second physiological response may also be referred to as a delayed physiological response elicited by the delivery of the first stimulation therapy according to the therapy program during the first time period.

As described above, in some examples the stimulation parameters according to which therapy delivery module 52 delivers stimulation during the first time periods may define a stimulation intensity below a threshold intensity. As described above, the threshold intensity may be a physiological intensity threshold or a therapeutic intensity threshold.

Figure 6:
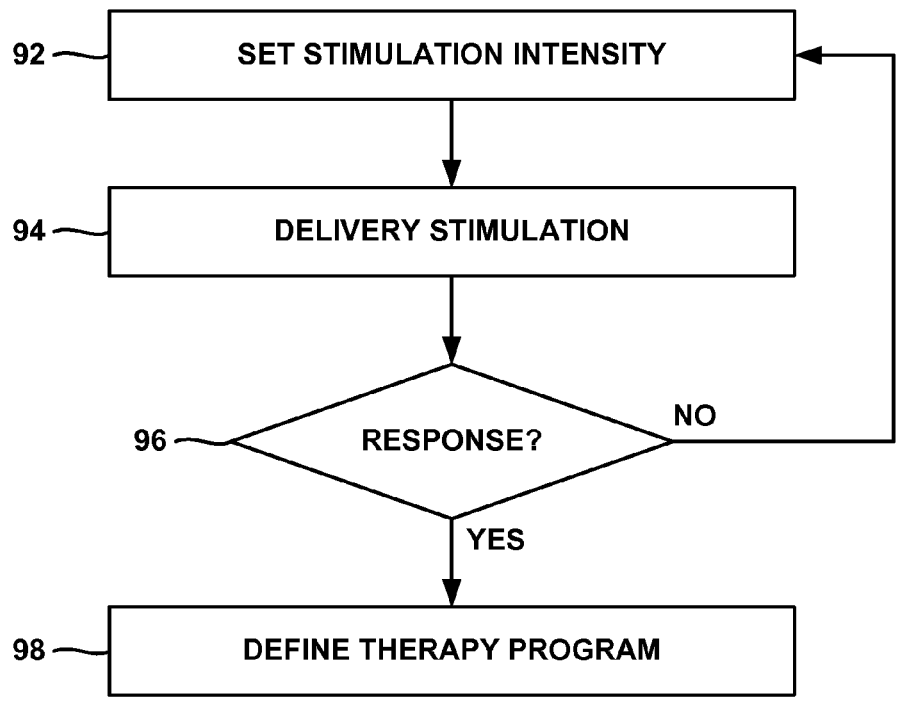
FIG. 6 is a flow diagram of an example technique for determining a threshold stimulation intensity and defining stimulation parameters that result in a stimulation intensity below the threshold intensity.

FIG. 6 is a flow diagram of an example technique by which control module 50 may determine the threshold intensity and define stimulation parameters that result in an intensity below the threshold. In some examples, control module 50 may implement the technique illustrated in FIG. 6 automatically, e.g., without user intervention or control after initiating the technique. In other examples, control module 50 may implement the technique illustrated in FIG. 6 under control of a user, such as a clinician, who controls control module 50 via programmer 24.

Control module 50 first may set stimulation parameter values such that the stimulation parameter values define a relatively low stimulation intensity, e.g., an intensity below an expected threshold intensity (92). These initial stimulation parameter values may be selected by a clinician in some examples. In addition, in some examples, control module 50 controls therapy delivery module 52 to deliver stimulation to patient 14 in the form of electrical pulses, and the stimulation parameters include at least one of a voltage amplitude, a current amplitude, a pulse width, a pulse rate, or a duty cycle. In other examples, control module 50 and therapy delivery module 52 deliver stimulation to patient 14 in the form of an electrical waveform, and the stimulation parameters include at least one of a voltage amplitude, a current amplitude, a frequency, a waveform shape, or a duty cycle.

In either case, control module 50 sets the stimulation parameters to respective values to define a stimulation intensity, and causes therapy delivery module 52 to delivery stimulation to patient 14 according to the stimulation parameters (94). During therapy delivery or after therapy delivery module 52 delivers stimulation to patient 14, control module 50 monitors for a threshold physiological response (also referred to as a "physiological response" in some cases) or a threshold therapeutic response (also referred to as a "therapeutic response") of patient 14 (96). In some examples, such as when an electrode 29 is implanted proximate to a spinal nerve (e.g., an S3 nerve), the threshold physiological response may include a flexing of a toe of patient 14 or an anal sphincter of patient 14. In such examples, patient 14 or a clinician may observe the threshold physiological response and indicate a presence or absence of a physiological response to control module 50 via programmer 24. In other examples, control module 50 may detect a threshold physiological response, such as a flexing of a muscle, via an EMG. In some examples, control module 50 may monitor a signal generated by electrodes 19 and/or 21 and may generate the EMG based on these signals. The particular physiological response that indicates the capture of a nerve by the stimulation may depend on the target tissue site.

A threshold therapeutic response may include, for example, an acute therapeutic response due to delivery of stimulation. For example, the threshold therapeutic response may include an acute (e.g., within about 30 or less from initiation of stimulation delivery) reduction in frequency of bladder contractions. Control module 50 may detect a frequency of bladder contractions by, for example, monitoring impedance of bladder 12 to detect contraction of bladder 12 based on signals received from impedance module 54 or monitoring signals received from sensor 22 to detect contraction of bladder 12 using, for example, changes in pressure of bladder 12.

When control module 50 does not detect a threshold physiological response or threshold therapeutic response within a predetermined time period during or immediately after delivery of the stimulation according to the selected stimulation intensity ("NO" branch of block 96), e.g., via an input from a user or a signal from electrodes 19 and/or 21, control module 50 may adjust at least one stimulation parameter value to increase a stimulation intensity of the stimulation signal (92). For example, control module 50 may increase a voltage amplitude or a current amplitude to increase the stimulation intensity. Control module 50 then causes therapy delivery module 52 to deliver stimulation to patient 14 using the newly define stimulation parameter values (94). Whether control modules 50 determines whether the stimulation elicited a threshold physiological response or threshold therapeutic response during or immediately after delivery of the stimulation according to the selected stimulation intensity may be based on the type of stimulation delivered and the type of physiological response or therapeutic response that is expected.

Again, control module 50 monitors for a threshold physiological response or a threshold therapeutic response of patient 14 within a predetermined time period during or immediately after delivery of the stimulation according to the selected stimulation intensity (96). If control module 50 does not detect a threshold physiological response or a threshold therapeutic response ("NO" branch of block 96), control module 50 may again adjust at least one stimulation parameter value to increase a stimulation intensity of the stimulation signal (92). This process may repeat until control module 50 does detect a threshold physiological response or a threshold therapeutic response of patient 14 (96).

When control module 50 detects a threshold physiological response or a threshold therapeutic response of patient 14 ("YES" branch of block 96), control module 50 may proceed to define a set of stimulation parameter values for the therapy program 66 to be delivered to patient 14 during the first time period (98). In some examples, control module 50 does so in response to an input from a user, such as a clinician, via programmer 24. For example, control module 50 may transmit to programmer 24 the stimulation parameters used by therapy delivery module 52 for the stimulation which elicited the physiological response from patient 14. The clinician may then determine stimulation parameter values that define a stimulation intensity that is less than the threshold stimulation intensity. For example, the clinician may reduce a voltage or current amplitude to reduce the stimulation intensity. In some examples, the reduced stimulation intensity is between about 50% and about 100% of the threshold stimulation intensity, such as between about 50% and about 75% or between about 75% and about 100%. Thus, in some examples, the clinician may reduce the voltage or current amplitude to be about 40% and about 100% of the amplitude that resulted in the threshold stimulation intensity, such as between about 40% and about 75% of the amplitude value or between about 75% and about 100% of the amplitude value.

In other examples, control module 50 may automatically define a set of stimulation parameter values for the therapy program 66 to be delivered to patient 14 during the first time period (98). For examples, control module 50 may reduce a voltage or current amplitude to reduce the stimulation intensity. Again, in some examples, the reduced stimulation intensity is between about 50% and about 100% of the threshold stimulation intensity, such as between about 50% and about 75% or between about 75% and about 100%.

Although the technique illustrated in FIG. 6 has been described with reference to control module 50 and therapy delivery module 52 of IMD 16, in other examples, control module 70 of programmer 24 may perform at least some of the function ascribed to control module 50. For example, control module 70 may define a set of stimulation parameters that define the stimulation intensity (92) and transmit the set of stimulation parameters to control module 50 of IMD 16 via telemetry module 76 of programmer 24 and telemetry module 58 of IMD 16. Control module 50 may then control therapy delivery module 52 to deliver stimulation to patient 14 according to the stimulation parameters (94). In some examples, control module 70 of programmer 24 may then prompt the user via user interface 74 to input whether a physiological response of patient 14 to the stimulation was observed, e.g., flexing of a toe or anal sphincter. Based on this input, control module 70 may either adjust at least one of the stimulation parameters (92) and transmit the new parameters to control module 50 of IMD 16, or may automatically or under control of the user define stimulation parameters for use in the therapy program delivered by therapy delivery module 52.

Figure 7:
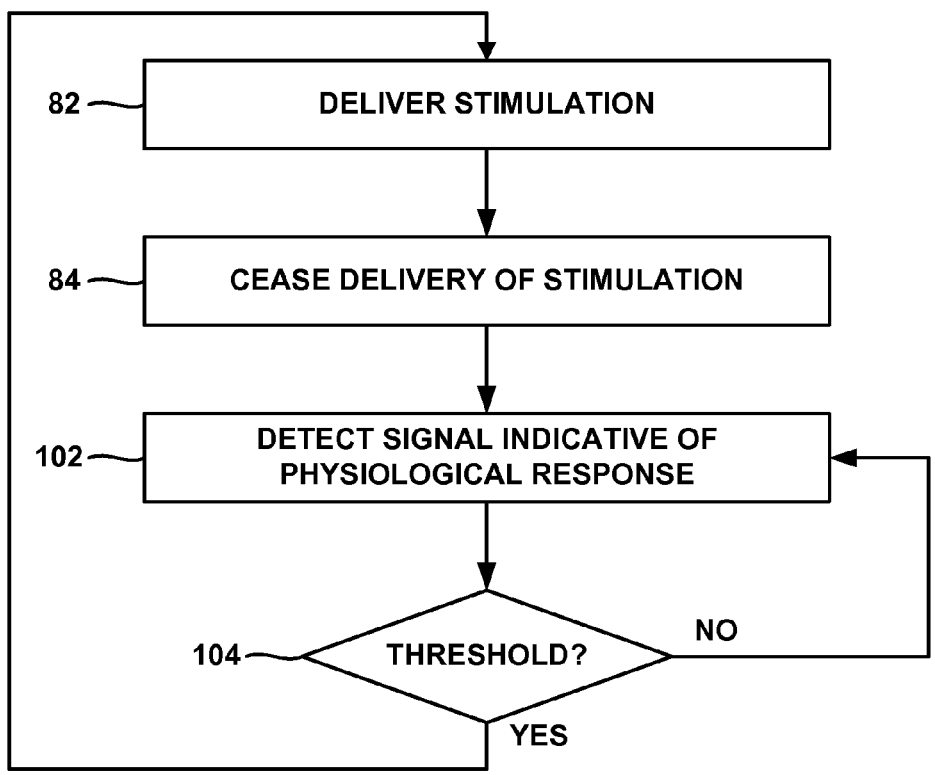
FIG. 7 is a flow diagram that illustrates an example technique for delivering stimulation therapy that includes a first time period during which an IMD delivers stimulation to the patient and a second time period during which the IMD does not deliver stimulation to the patient.

FIG. 7 is a flow diagram illustrating an example technique for delivering closed loop therapy including a first time period during which therapy delivery module 52 delivers stimulation to patient 14 and a second time period during which therapy delivery module 52 does not deliver stimulation to patient 14. In the example illustrated in FIG. 7, the duration of the second time period may be adjusted by control module 50 in response to an input received from sensor 22 or electrodes 19 and/or 21. In other examples, the duration of the second time period may be adjusted in response to another input, e.g., from a user such as patient 14 or a clinician or another sensing module of therapy system 10. In some examples, in addition to or as an alternative to adjusting the duration of the second time period, the duration of the first time period may be adjusted based on an input received by control module 50.

Control module 50 controls therapy delivery module 52 to deliver stimulation to patient 14 via electrodes 29 during a first time period, where the stimulation is defined by a therapy program (82). As described above, the stimulation therapy delivered during the first time period according to the therapy program may elicit substantially no inhibitory physiological response related to voiding in patient 14 during the first time period, or may elicit a first inhibitory physiological response related to voiding in patient 14 during the first time period. The therapy program may be selected, e.g., using the technique shown in FIG. 6. In some examples, the first inhibitory physiological response related to voiding includes a reduction in contraction frequency of bladder 12. In some examples, the duration of the first time period is greater than about 5 minutes, such as between about 5 minutes and about 20 minutes, or about 10 minutes.

In some examples, the stimulation parameters according to which therapy delivery module 52 delivers the stimulation therapy during the first time period define a stimulation intensity that is less than a threshold stimulation intensity, as describe with respect to FIG. 6. In other examples, the stimulation parameters define a stimulation intensity that is substantially equal to the threshold stimulation intensity, or is greater than the threshold stimulation intensity.

At the end of the first time period, control module 50 controls therapy delivery module 52 to cease delivering stimulation (84) and detects a signal indicative of a physiological response of patient 14 to the stimulation delivery according to the therapy program during the first time period (102). This physiological response may differ from the threshold physiological response used to determine the threshold intensity. Control module 50 can detect the signal indicative of the physiological response using any suitable technique. In some examples, control module 50 monitors contraction of bladder 12. In some examples, control module 50 may monitor impedance of bladder 12 to detect contraction of bladder 12 based on signals received from impedance module 54. In some implementations, control module 50 monitors impedance of bladder 12 for a predetermined duration of time within the second time period to detect contractions of bladder 12.

In other examples, control module 50 may monitor signals received from sensor 22 to detect contraction of bladder 12. For example, sensor 22 may be a pressure sensor for detecting changes in pressure of bladder 12, which control module 50 may correlate to contractions of bladder 12. Control module 50 may determine a pressure value based on signals received from sensor 22 and compare the determined pressure value to a threshold value stored in bladder data 69 to determine whether the signal is indicative of a contraction of bladder 12.

Regardless of the manner by which control module 50 monitors contraction of bladder 12, control module 50 may determine the contraction frequency of bladder 12 by determining a number of contractions of bladder 12 in the predetermined duration of time. Control module 50 then may compare the contraction frequency of bladder 12 to a threshold contraction frequency or a baseline contraction frequency (104). As described with respect to FIG. 3, the baseline contraction frequency may be contraction frequency of bladder 12 at a time prior to delivery of stimulation therapy by therapy delivery module 52 (e.g., prior to initiation of the technique illustrated in FIG. 7) and when no efficacious effects of stimulation therapy are observed. A threshold contraction frequency may be a predetermined percentage of the baseline contraction frequency or a percentage of the baseline contraction frequency input by a user via programmer 24. As one example, the threshold frequency may be between approximately 75% and approximately 100% of the baseline contraction frequency. As another example, the threshold contraction frequency may instead be based on clinical data collected from a plurality of patients.

When control module 50 determines that the contraction frequency of bladder 12 is above the threshold value or within a predetermined amount of the baseline contraction frequency, control module 50 may cause therapy delivery module 52 to initiate delivery of stimulation to patient 14 (82). However, when control module 50 determined that the contraction frequency of bladder 12 is below the threshold value or within a predetermined amount of the baseline contraction frequency, control module 50 may continue to detect the signal representing the physiological response (102) until the bladder contraction frequency of interest is detected. Delivery of stimulation at a time period prior to the detection of the bladder contraction frequency that is above the threshold value or within a predetermined amount of the baseline contraction frequency may not provide a significant therapeutic advantage to patient 14, because the bladder contraction frequency may indicate that the therapeutic effects of the delivery of stimulation according to the therapy program during the immediately preceding first time period are still present. In this way, delivery of stimulation according to the technique shown in FIG. 7 may be efficient because it may limit the extent to which therapy that may not have a significant impact on patient 14 is delivered.

The steps of delivering the first stimulation therapy and monitoring the patient to detect contractions of bladder 12 are illustrated in FIG. 7 as being sequential, but it should be understood that these steps may be performed simultaneously instead of sequentially. For example, control module 50 may detects a signal representing a physiological response (102) while controlling therapy delivery module 52 to delivery stimulation therapy (82) and after controlling therapy delivery module 52 to cease delivery of stimulation therapy (84).

Figure 8:
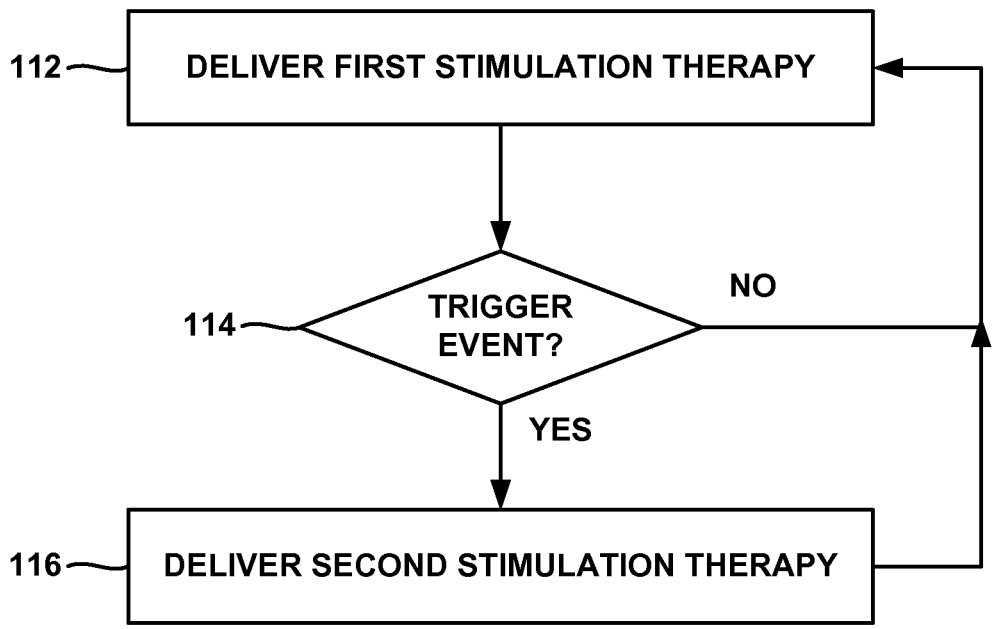
FIG. 8 is a flow diagram that illustrates an example technique for delivering first and second stimulation therapies to a patient to manage a bladder dysfunction.

FIG. 8 is a flow diagram illustrating an example technique for delivering first and second stimulation therapies to a patient to manage fecal or urinary urgency or incontinence. Under control of control module 50, therapy delivery module 52 of IMD 16 delivers first stimulation therapy to patient 14 (112). In some examples, control module 50 initiates the delivery of the first stimulation therapy by therapy delivery module 52 upon activation of chronic therapy delivery by the clinician. Therapy delivery module 52 delivers the first stimulation therapy chronically, e.g., periodically for an extended period of time, such as hours, days, or weeks.

Control module 50 monitors a patient condition via a sensor to determine whether a trigger event is detected (114). Examples of trigger events that may be detected include, but are not limited to, bladder contraction exceeding (e.g., greater than or equal to) a threshold level, abnormal detrusor muscle activities (e.g., as indicated by an EMG), patient activity level exceeding a threshold level, patient posture state, and patient input. As previously described, control module 50 may monitor bladder impedance, bladder pressure, pudendal or sacral afferent nerve signals, a urinary sphincter EMG, or any combination thereof to detect changes in bladder contraction.

The steps of delivering the first stimulation therapy and monitoring the patient to detect a trigger event are illustrated in FIG. 8 as being sequential, but it should be understood that these steps may be performed simultaneously instead of sequentially. As an example, therapy delivery module 52 may deliver the first stimulation therapy to patient 14 for an extended period of time. During the extended period of time, control module 50 may periodically monitor patient 14 to detect a trigger event. In other examples, control module 50 may monitor patient 14 substantially continuously.

If control module 50 does not detect a trigger event ("NO" branch of block 114), therapy delivery module 52 continues to deliver the first stimulation therapy (112) without delivering the second stimulation therapy (116). On the other hand, if control module 50 detects a trigger event ("YES" branch of block 114), control module 50 causes therapy delivery module 52 to deliver the second stimulation therapy (116). The first and second stimulation therapies may be delivered substantially simultaneously (e.g., during a first time period of the first stimulation therapy) or the second stimulation therapy may be delivered during a second time period of the first stimulation therapy. As previously described, the second stimulation therapy elicits a different physiological effect than the first stimulation therapy. For example, the second stimulation therapy may elicit a movement of muscles of the patient that provides a specific functional result, such as a contraction of the urinary or anal sphincter of a patient.

In some examples, therapy delivery module 52 delivers the second stimulation therapy (116) for a predetermined period of time, e.g., about 10 seconds to about 50 seconds. The duration of the predetermined period of time may be selected such that an imminent involuntary voiding event is suppressed. In some examples, after the predetermined period of time, control module 50 determines whether the patient condition that triggered the delivery of the second stimulation therapy is still present. For example, control module 50 may determine whether the bladder contractions are still greater than or equal to a threshold value. If the patient condition that triggered the delivery of the second stimulation therapy is still present, control module 50 may cause the therapy delivery module 52 to deliver the second stimulation therapy (116) again for another predetermined period of time.

In other examples, therapy delivery module 52 delivers the second stimulation therapy (116) for a period of time controlled by patient 14. For example, patient 14 may control the duration of the second stimulation therapy by interacting with programmer 24, e.g., by pressing a button on a keypad or a touch screen, or by interacting directly with IMD 16 (e.g., by tapping skin superior to the implanted IMD 16). A maximum therapy period for patient controlled stimulation may be approximately 3 minutes, although other time ranges are contemplated.

After completion of the delivery of the second stimulation therapy, therapy delivery module 52 continues to deliver the first stimulation therapy (112) and the technique shown in FIG. 8 is repeated as necessary. Thus, IMD 16 delivers the first stimulation therapy and, when triggered, delivers the second stimulation therapy for a limited duration of time (e.g., shorter in duration than the duration of time that the first stimulation therapy is delivered). That is, IMD 16 delivers chronic stimulation for an extended period of time via the first stimulation therapy, and, when necessary or desirable, delivers the second stimulation therapy. The second stimulation therapy is provided for a comparatively short period of time within the extended period of time during which the chronic therapy delivery is provided.

In this way, IMD 16 provides responsive stimulation to manage bladder dysfunction. Delivering the second stimulation therapy upon detection of a trigger event, rather than on a substantially regular basis, may help reduce muscle fatigue by limiting the amount of the second stimulation therapy provided to patient 14. In addition, implementing the second stimulation therapy only when needed may help conserve power of power source 60 of IMD 16. Conserving power may help elongate the useful life of IMD 16.

Figure 9:
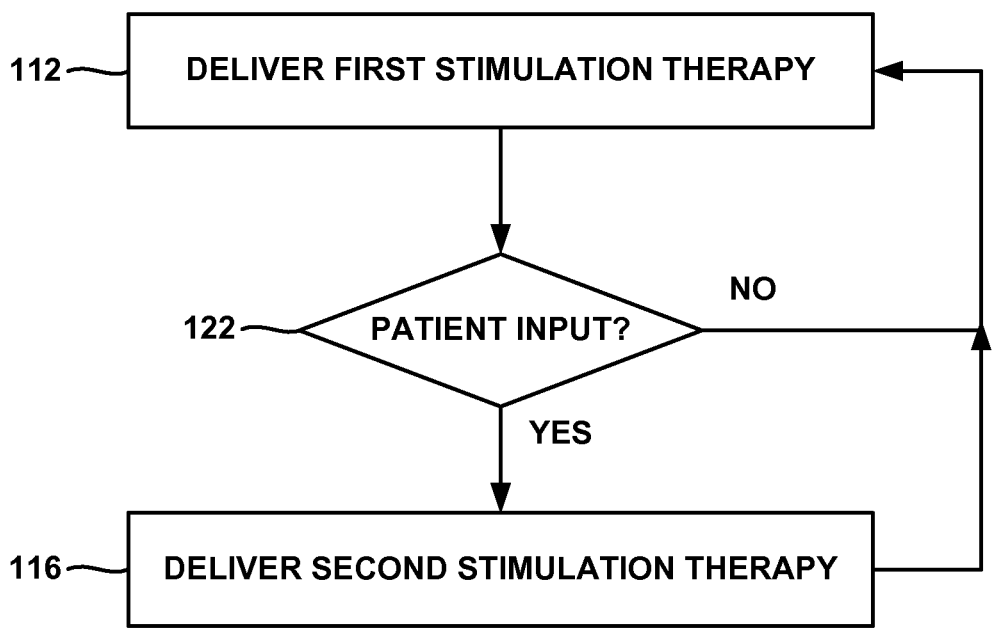
FIG. 9. is a flow diagram illustrating an example technique for delivering stimulation therapy to a patient to manage a bladder dysfunction.

FIG. 9 is a flow diagram illustrating an example technique for delivering a stimulation therapy to patient 14 to manage bladder dysfunction, where the technique includes delivering a first stimulation therapy and, upon receiving patient input, delivering a second stimulation therapy. The example technique shown in FIG. 9 is an example of the technique shown in FIG. 8. That is, the event that triggers the delivery of the second stimulation therapy in FIG. 9 is patient input.

In accordance with the technique shown in FIG. 9, IMD 16 delivers first stimulation therapy to patient 14 (112). Upon receiving patient input ("YES" brand of block 122), control module 50 of IMD 16 controls therapy delivery module 52 to generate and deliver the second stimulation therapy to patient 14 to generate the second physiological response that helps prevent an involuntary voiding event.

As previously indicated, patient 14 may provide the patient input (122) via programmer 24, e.g., by activating a button on a keypad or select an icon using a touch screen of programmer 24. Programmer 24 wirelessly communicates the patient input to IMD 16 via the respective telemetry modules 76, 58. In other examples, patient 14 may provide input indicating the delivery of the second stimulation therapy is desirable via IMD 16. For example, IMD 16 may include a motion sensor that detects movement of IMD 16 and patient 14 may provide input by tapping the skin proximate IMD 16 in a predetermined pattern, such that IMD 16 detects the movement and characterizes the movement as patient input.

When IMD 16 does not receive patient input that activates the delivery of the second stimulation therapy ("NO" branch of block 122), IMD 16 continues to deliver the first stimulation therapy (112) and monitor for patient input.

EXAMPLES

Example 1

Figure 10:
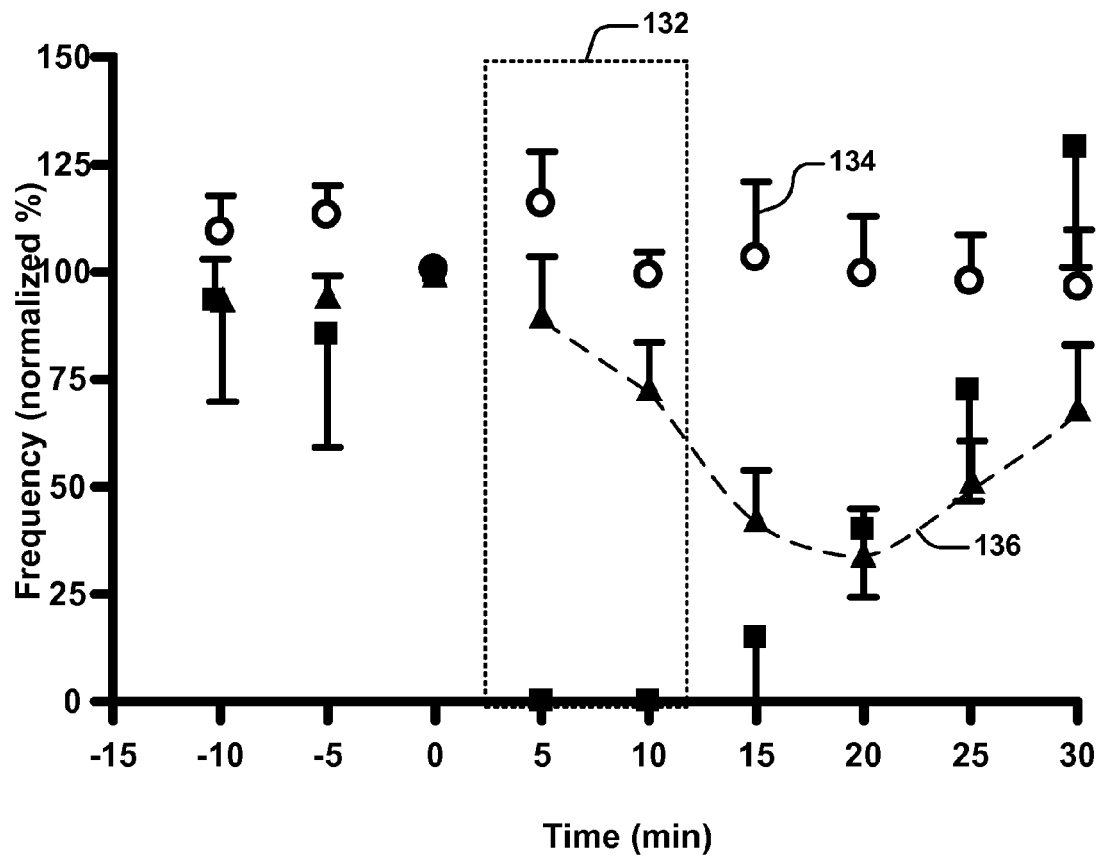
FIGS. 10-12 are graphs that illustrate examples of changes in bladder contraction frequency in response to electrical stimulation.

FIG. 10 is a graph that illustrates a change in bladder contraction frequency in response to electrical stimulation.

The data illustrated in FIG. 10 was obtained from a plurality of tests performed on laboratory rats. During the tests, bladder contractions of one or more test subjects were observed during an approximately 45 minute period (i.e., −15 min to 30 min). During observation, the test subject was provided with electrical stimulation to a spinal nerve for a period of time, as illustrated at 132. For each test run (i.e., each 45 minute observation), a frequency of bladder contractions was determined at approximately 5 minute intervals. The determined frequencies of bladder contractions were then normalized (i.e., divided by) by a frequency of bladder contractions of the test subject at time zero. The normalized bladder contraction frequencies are graphed in FIG. 10.

The graph illustrated in FIG. 10 plots frequency versus time. Frequency (normalized %) indicates a frequency of bladder contraction relative to the frequency of bladder contractions of the test subject at time zero. Frequency (normalized %) ranges from 0% to 150%.

In the graph shown in FIG. 10, the intensity of stimulation delivered to the test subject is indicated by the shape of the data point. The circle data points indicate measurement of contractions in subjects that did not receive electrical stimulation (the control group). Accordingly, the circle data points represent a bladder contraction frequency at approximately 100% normalized frequency. The triangle data points indicate measurement of bladder contractions in subjects that received stimulation at an amplitude of the threshold stimulation intensity for the test subjects (mean of 0.16 mA), a frequency of about 10 Hz, and a wavelength of about 100 microseconds (μs), which was approximately equal to the mean threshold stimulation intensity for the test subjects. The square data points indicate measurement of contractions in subjects that received stimulation at an intensity greater than a threshold stimulation intensity, e.g., at an amplitude of about 0.6 mA, a wavelength of about 100 μs, and a frequency of about 10 Hz. Each of the data points (i.e., circle, square, and triangle) include an amount of variation. The variation bars, e.g., illustrated in one example at 134, are included to show variations among measurements.

The square data points (e.g., greater than threshold intensity stimulation) indicate a frequency substantially equal to zero during delivery of high intensity stimulation. In other words, it was observed that the bladder contraction frequency was reduced to substantially zero upon delivery of above-threshold intensity stimulation and remained zero during the delivery of the high intensity stimulation (i.e., during stimulation period 132). Upon cessation of the above-threshold intensity stimulation (i.e., immediately after stimulation period 132), bladder contraction frequency begins to increase and recovers toward the control frequency, i.e., toward the bladder contraction frequency observed when no stimulation therapy is delivered.

The triangle data points define a curve, illustrated by the dotted line 136, which illustrates the approximate response produced by threshold-intensity stimulation. The decreasing trend in the curve from approximately 100% to less than 50% may illustrate the response of the bladder to the threshold-intensity stimulation. The curve indicates that reduction in bladder contraction frequency is not pronounced, but may be present, during delivery of the threshold-intensity stimulation (i.e., during stimulation period 132). However, a reduction in bladder contraction frequency is greater after cessation of the threshold-intensity stimulation. Specifically, bladder contractions are reduced to between about 25% and about 50% of the control frequency.

Example 2

Figure 11:
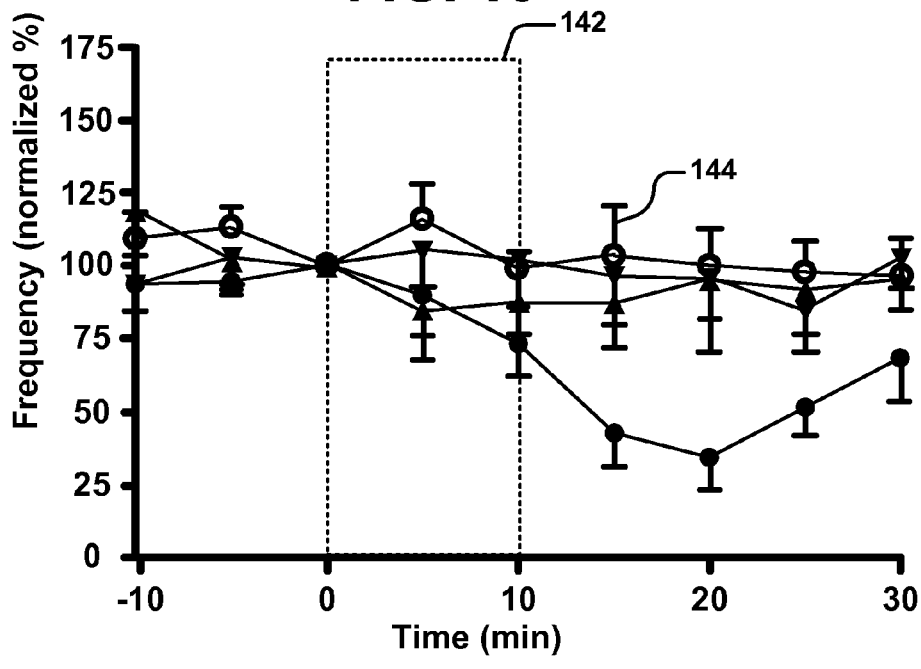

FIG. 11 is a graph that illustrates a change in bladder contraction frequency in response to electrical stimulation.

The data illustrated in FIG. 11 was obtained from a plurality of tests performed on laboratory rats. During the tests, bladder contractions of twenty-six test subjects were observed during an approximately 40 minute period (i.e., −10 min to 30 min). During observation, the test subject was provided with electrical stimulation to a spinal nerve for about 10 minutes, as illustrated by stimulation period 142. For each test run (i.e., each 40 minute observation), a frequency of bladder contractions was determined at approximately 5 minute intervals. The determined frequencies of bladder contractions were then normalized (i.e., divided by) by a frequency of bladder contractions of the test subject at time zero. The normalized bladder contraction frequencies are graphed in FIG. 11.

Intensity of stimulation delivered to the test subject is indicated by the shape of the data point. The open-circle data points indicate measurement of contractions in subjects that did not receive electrical stimulation (the control group). Accordingly, the open-circle data points are equal to approximately 100% normalized frequency. The closed-circle data points indicate measurement of contractions in ten subjects that received stimulation at a current of about 0.16 mA, a wavelength of about 100 µs, and a frequency of about 10 Hz. The upward-oriented triangle data points (i.e., the triangles with points oriented upward) indicate measurement of contractions in nine subjects that received stimulation at current of about 0.13 mA, a wavelength of about 100 µs, and a frequency of about 20 Hz. The downward-oriented triangle data points (i.e., the triangles with points oriented downward) indicate measurement of contractions in seven subjects that received stimulation at a current of about 0.24 mA, a wavelength of about 100 µs, and a frequency of about 1 Hz. Each of the data points includes an amount of variation. The variation bars, e.g., illustrated in one example at 144, are included to show variations among measurements.

The upward-oriented triangle data points and the downward-oriented triangle data points indicate that the stimulation delivered during stimulation period 142 elicited substantially no change in the bladder contraction frequency, either during or after stimulation.

The closed-circle data points indicate that the stimulation delivered during stimulation period 142 provided some inhibition of bladder contraction frequency during the time when stimulation was provided. Additionally, the stimulation at about 0.16 mA and about 10 Hz elicited a greater inhibition of bladder contraction frequency after the stimulation was ceased, i.e., after stimulation period 142. For example, about 10 minutes after stimulation was ceased (i.e., at the approximately 20 minute mark), the bladder contraction frequency was reduced to between about 25% and about 50% of the control frequency. Accordingly, FIG. 11 illustrates that relatively low intensity stimulation at a frequency of about 10 Hz may elicit a greater physiological response after stimulation is ceased than when the stimulation is being delivered to the patient.

Example 3

Figure 12:
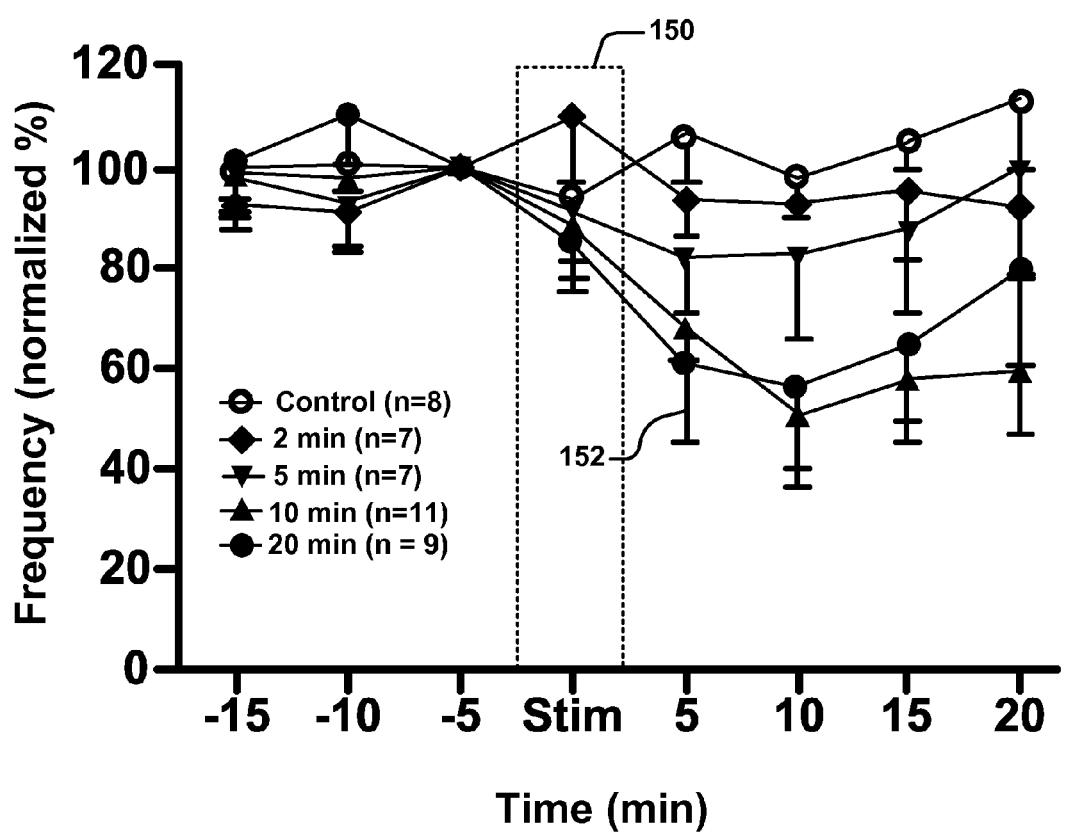

FIG. 12 is a graph that illustrates a change in bladder contraction frequency in response to electrical stimulation for different durations of stimulation. The data illustrated in FIG. 12 was obtained from a plurality of tests performed on Sprague-Dawley female laboratory rats. During the tests, bladder contractions of one or more test subjects were observed during a period prior to, during, and after stimulation (labeled in FIG. 12 as −15 min to 20 min). The key in FIG. 12 illustrates the number of rats (n) tested for each condition. By considering two factors (inhibitory effects to different time points in control and stimulated rats), the inhibitory effects by stimulation is statistically significant. Such analysis has been tested by 2-way ANOVA. The null hypothesis is that stimulation does not affect the bladder contractions. There is less than 5% chance that the null hypothesis is true. Such results were repeatable in many rats, as indicated by the n value. For example, 8 rats, 7 rats, 7 rats, 11 rats, and 9 rats were tested with electrical stimulation for 1, 2, 5, 10 and 20 min, respectively.

During observation, the test subject was provided with electrical stimulation to a spinal nerve for different durations of time. The data in FIG. 12 has been adjusted so that the entire duration of stimulation is represented as a single point, at "Stim" along the x-axis of FIG. 12. In addition, box 150 indicates the point in time of the electrical stimulation delivery for each group. This allows the onset and offset of the respective stimulation periods to be aligned in FIG. 12. For each test run (i.e., each observation period), a frequency of bladder contractions was determined at approximately 5 minute intervals. The determined frequencies of bladder contractions were then normalized (i.e., divided by) by a frequency of bladder contractions of the test subject at −5 minutes. The normalized bladder contraction frequencies are graphed in FIG. 12.

The duration of the stimulation period delivered to the test subject is indicated by the shape of the data point. The open-circle data points indicate measurement of contractions in subjects that did not receive electrical stimulation (the control group). Accordingly, the open-circle data points are equal to approximately 100% normalized frequency. The diamond data points indicate measurement of contractions in subjects that received stimulation for about 2 minutes. The stimulation was delivered at a frequency of 10 Hz and an amplitude that resulted in the threshold stimulation intensity for each test subject (mean of about 0.21 mA). As described in this disclosure, the physiological threshold stimulation intensity is the stimulation intensity at which stimulation causes a certain acute physiological response, e.g., a motor threshold, a stimulation perception threshold, a non-therapeutic effect, or a detected physiological response, such as nerve action potentials. In the example of FIG. 12, the current amplitude was selected such that the stimulation intensity met the motor threshold intensity that induced an acute motor response, i.e., muscle twitch, in the subject. However, this stimulation intensity was insufficient to cause the desired therapeutic effect during stimulation delivery The downward-oriented triangle data points (i.e., the triangles with points oriented downward) indicate measurement of contractions in subjects that received stimulation for about 5 minutes. The stimulation was delivered at a frequency of 10 Hz and an amplitude that resulted in the threshold stimulation intensity for each test subject (mean of about 0.21 mA). The upward-oriented triangle data points (i.e., the triangles with points oriented upward) indicate measurement of contractions in subjects that received stimulation for about 10 minutes. The stimulation was delivered at a frequency of 10 Hz and an amplitude that resulted in the threshold stimulation intensity for each test subject (mean of about 0.16 mA). The closed-circle data points indicate measurement of contractions in subjects that received stimulation for about 20 minutes. The stimulation was delivered at a frequency of 10 Hz and an amplitude that resulted in the threshold stimulation intensity for each test subject (mean of about 0.21 mA). Each of the data points includes a standard deviation bar to indicate the amount of variation between measurements. The standard deviation bars, e.g., illustrated in one example as standard deviation bar 144, are included to indicate the standard deviation between measurements used to produce each data point.

With respect to the downward-oriented triangle data points and the diamond data points, the stimulation elicited substantially no change in the bladder contraction frequency, either during or after stimulation.

With respect to the closed-circle data points and the upward-oriented triangle data points, the stimulation may have provided some inhibition of bladder contraction frequency during the time when stimulation was provided (20 minutes and 10 minutes, respectively). Additionally, the 10-minute and 20-minute stimulations each elicited a greater inhibition of bladder contraction frequency after the stimulation was ceased. For example, about 10 minutes after stimulation was ceased (i.e., at the 10 minute mark), the bladder contraction frequency was reduced to between about 40% and about 60% of the control frequency for each of the 10-minute stimulation and the 20-minute stimulation. Accordingly, FIG. 12 illustrates that relatively low intensity stimulation at a frequency of about 10 Hz may elicit a greater physiological response after stimulation is ceased than when the stimulation is being delivered to the patient. Indeed, little to no physiological response was detected during the delivery of stimulation within box 150.

The techniques described in this disclosure, including those attributed to IMD 16, programmer 24, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. While the techniques described herein are primarily described as being performed by control module 50 of IMD 16 and/or control module 70 of programmer 14, any one or more parts of the techniques described herein may be implemented by a processor of one of IMD 16, programmer 14, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

The invention claimed is:

1. A medical system comprising:
a therapy delivery module configured to generate and deliver electrical stimulation therapy to a patient; and
a control module configured to:
control the therapy delivery module to deliver electrical stimulation at a first stimulation intensity for a duration of a first time period, wherein the first time period is at least about 5 minutes, and wherein the first stimulation intensity is between about 50% and about 100% of a threshold stimulation intensity;
control the therapy delivery module to cease delivering electrical stimulation at the first stimulation intensity for a duration of a second time period and deliver electrical stimulation at a second stimulation intensity for the duration of the second time period, wherein the second time period immediately follows the first time period, wherein the second stimulation intensity is less than the first stimulation intensity, wherein the electrical stimulation elicits an inhibitory physiological response related to voiding in the patient during the second time period, and wherein the second time period is at least about 5 minutes; and
control the therapy delivery module to cease delivering electrical stimulation at the second stimulation intensity for a duration of a third time period and begin delivering electrical stimulation at the first stimulation intensity for the duration of the third time period, wherein the third time period immediately follows the second time period.

2. The medical system of claim 1, wherein the control module is further configured to:
determine the threshold stimulation intensity, wherein the threshold stimulation intensity is defined by a plurality of stimulation parameters and elicits a physiological response in the patient indicative of electrical capture of a nerve; and
change at least one of the plurality of stimulation parameters defining the threshold stimulation intensity to define the first stimulation intensity.

3. The medical system of claim 1, wherein the electrical stimulation at the first stimulation intensity elicits substantially no inhibitory physiological response in the patient during the first time period.

4. The medical system of claim 1, wherein the inhibitory physiological response related to voiding comprises a first inhibitory physiological response related to voiding, and wherein the electrical stimulation elicits a second inhibitory physiological response related to voiding in the patient during the first time period, and wherein the first inhibitory physiological response is greater than the second inhibitory physiological response.

5. The medical system of claim 4, wherein the first and second inhibitory physiological responses related to voiding each comprises a reduction in bladder contraction frequency.

6. The medical system of claim 1, wherein the duration of the first time period is less than about 20 minutes.

7. The medical system of claim 1, wherein the threshold stimulation intensity comprises a physiological intensity threshold or a therapeutic intensity threshold.

8. A method comprising:
controlling, by a control module, a therapy delivery module to deliver electrical stimulation at a first stimulation intensity to a patient for a duration of a first time period, wherein the first time period is at least about 5 minutes, and wherein the first stimulation intensity is between about 50% and about 100% of a threshold stimulation intensity;

controlling, by the control module, the therapy delivery module to cease delivering electrical stimulation at the first stimulation intensity for a duration of a second time period and deliver electrical stimulation at a second stimulation intensity to the patient for the duration of the second time period, wherein the second time period immediately follows the first time period, wherein the second stimulation intensity is less than the first stimulation intensity, wherein the electrical stimulation elicits a second inhibitory physiological response related to voiding in the patient during the second time period, and wherein the second time period is at least about 5 minutes; and controlling, by the control module, the therapy delivery module to cease delivering electrical stimulation at the second stimulation intensity for a duration of a third time period and begin delivering electrical stimulation at the first stimulation intensity to the patient for the duration of the third time period, wherein the third time period immediately follows the second time period.

9. The method of claim 8, further comprising:

determining, by the control module, the threshold stimulation intensity, wherein the threshold stimulation intensity is defined by a plurality of stimulation parameters and elicits a physiological response in the patient indicative of electrical capture of a nerve; and changing, by the control module, at least one of the plurality of stimulation parameters defining the threshold stimulation intensity to define the first stimulation intensity.

10. The method of claim 8, wherein the electrical stimulation at the first stimulation intensity elicits substantially no inhibitory physiological response in the patient during the first time period.

11. The method of claim 8, wherein the inhibitory physiological response related to voiding comprises a first inhibitory physiological response related to voiding, and wherein the electrical stimulation elicits a second inhibitory physiological response related to voiding in the patient during the first time period, and wherein the first inhibitory physiological response is greater than the second inhibitory physiological response.

12. The method of claim 8, wherein the first and second inhibitory physiological responses related to voiding each comprises a reduction in bladder contraction frequency.

13. The method of claim 8, wherein the duration of the first time period is less than about 20 minutes.

14. The method of claim 8, wherein the threshold stimulation intensity comprises a physiological intensity threshold or a therapeutic intensity threshold.

* * * * *